US011006869B2

(12) United States Patent
Huang et al.

(10) Patent No.: US 11,006,869 B2
(45) Date of Patent: May 18, 2021

(54) TRANS-ABDOMINAL NON-INVASIVE FETAL BLOOD OXYGEN SATURATION DETECTION DEVICE

(71) Applicant: BEIJING Weitexing Technology Co. Ltd, Beijing (CN)

(72) Inventors: Wen Huang, Beijing (CN); Yixiang Wang, Beijing (CN)

(73) Assignee: BEIJING Weitexing Technology Co. Ltd, Beijing (CN)

( * ) Notice: Subject to any disclaimer, the term of this patent is extended or adjusted under 35 U.S.C. 154(b) by 322 days.

(21) Appl. No.: 16/133,765

(22) Filed: Sep. 18, 2018

(65) Prior Publication Data
US 2019/0261898 A1    Aug. 29, 2019

(30) Foreign Application Priority Data

Feb. 28, 2018  (CN) .......................... 201810169917.2
Feb. 28, 2018  (CN) .......................... 201810170444.8
Feb. 28, 2018  (CN) .......................... 201810170447.1

(51) Int. Cl.
*A61B 5/1455*    (2006.01)
*A61B 5/1464*    (2006.01)
(Continued)

(52) U.S. Cl.
CPC .......... *A61B 5/1464* (2013.01); *A61B 5/0064* (2013.01); *A61B 5/14551* (2013.01);
(Continued)

(58) Field of Classification Search
CPC .............. A61B 5/1455; A61B 5/14551; A61B 5/14552; A61B 5/1464; A61B 5/4362; A61B 5/6823
See application file for complete search history.

(56) References Cited

U.S. PATENT DOCUMENTS 9,757,058 B2 *   9/2017  Ray ................... A61B 5/14552
2004/0116789 A1 *  6/2004  Boas .................. A61B 5/14542
                                                                600/338

(Continued)

FOREIGN PATENT DOCUMENTS

CN           103381094 B      1/2015

*Primary Examiner* — Eric F Winakur
(74) *Attorney, Agent, or Firm* — Ostrolenk Faber LLP

(57)            ABSTRACT

A trans-abdominal non-invasive fetal blood oxygen saturation detection device comprises a trans-abdominal fetal oximeter and a signal detection assembly connected to the trans-abdominal fetal oximeter. The trans-abdominal oximeter comprises a signal processing controller. The signal detection assembly comprises a light-emitting light source device and a light receiving device, wherein the light-emitting light source device, the light receiving device and a reference signal detection device are all connected to the signal processing controller. The light-emitting light source device irradiates two or more different wavelengths of light into the abdominal cavity of a pregnant woman. The light receiving device comprises a plurality of light receivers respectively placed at a plurality of different positions outside the abdominal cavity of the pregnant woman, and is configured to collect a plurality of optical signals related to the fetal blood oxygen saturation, which are scattered and reflected back from the abdominal cavity of the pregnant woman through the plurality of light receivers, synthesize the optical signals into an optical signal sum related to the fetal blood oxygen saturation and then output it to the signal processing controller, such that the intensity of the received optical signals is improved.

18 Claims, 13 Drawing Sheets

(51) Int. Cl.
*A61B 5/00* (2006.01)
*A61B 5/024* (2006.01)
*A61B 5/288* (2021.01)

(52) U.S. Cl.
CPC ......... *A61B 5/4362* (2013.01); *A61B 5/02411* (2013.01); *A61B 5/288* (2021.01); *A61B 2562/0233* (2013.01)

(56) References Cited

U.S. PATENT DOCUMENTS

2009/0281402 A1* 11/2009 Chance .............. A61B 5/14553 600/328
2011/0218413 A1 9/2011 Wang et al. .................. 600/324

* cited by examiner

TRANS-ABDOMINAL NON-INVASIVE FETAL BLOOD OXYGEN SATURATION DETECTION DEVICE

TECHNICAL FIELD

The present invention relates to the technical field of blood oxygen saturation detection in medical devices, and more particularly, to a trans-abdominal non-invasive fetal blood oxygen saturation detection device.

BACKGROUND ART

Late pregnancy, as well as labor and delivery stages can be of a dangerous time phase for pregnant women and fetuses. It is possible to cause insufficient oxygen in the fetal blood to further result in fetal brain damage or death if the fetal umbilical cord becomes distorted in an unfavorable position, the placenta is prematurely separated, or pregnant women and fetuses suffer some diseases. Clinically, a physiological index, i.e., the saturation of pulse oximetry (SpO2) is used to indirectly monitor the human body, including the oxygen content in the fetal blood.

At present, fetal heart rate and heart sound monitors have been widely applied to the monitoring of fetal physiological status. Since the fetal oxygen supply is implemented by maternal delivery from the placenta, rather than fetus's own breathing, the fetal blood oxygen saturation can reflect the oxygen concentration in the blood more accurately, and thus is of a physiological index that reflects the fetal life status more directly. The clinical significance of detecting the fetal SpO2 is to directly reflect the oxygenation status of the fetus, thereby confirming the life status of the fetus in the maternal body to reduce the mortality of perinatal infants and the disability rate of newborns. In 2000, the US FDA approved an instrument (produced by Nellcor in the United States) for measuring the fetal blood oxygen saturation by placing a sensor in the uterus, and hereby the medical personnel needed to put the optical sensor deep into the uterus of a pregnant woman and directly measured the fetal blood oxygen saturation index from the fetal body surface. These methods and instruments are not suitable for long-term, continuous detection of the fetal blood oxygen saturation, and are further not suitable for perinatal monitoring of the fetus. Because there is currently no effective instrument device for detecting the fetal blood oxygen saturation non-invasively, medical personnel often rely only on a fetal heart rate monitoring instrument. However, the widely used fetal heart rate monitoring can detect the fetal suffocation sensitively, but cannot reflect the suffocation premonition in advance owing to low specificity. Due to the relatively low specificity of fetal heart monitoring, doctors lack sufficient understanding of the overall status of the fetus, such as whether a caesarean section is needed, when a caesarean section is initiated, and urgent medical decisions must be made without sufficient knowledge. Thus, on the one hand, doctors are likely to misdiagnose and delay the timing of taking necessary measures; on the other hand, doctors tend to be too cautious, resulting in an increase in many unnecessary interventions for the caesarean section, thereby not only increasing the risk of surgery and complications of maternal delivery, but also increasing social and family economic burdens from the consequent unnecessary high medical costs.

The inventors of the present invention provide a detection system and a detection method for monitoring the fetal pulse blood oxygen saturation non-invasively in Chinese Patent ZL201310182965.2 (Fetal Blood Oxygen Saturation Detection System and Method) (US Patent US2011/0218413A1), in which a fetal pulse blood oxygen saturation photoelectric sensor placed outside the body of a pregnant woman is used for the first time. During the detection process, it is not necessary to go deep into an abdominal cavity of the pregnant woman, and also not necessary to apply the photoelectric sensor to a specific position of the fetus, thereby really realizing the trans-abdominal non-invasive detection of the fetal blood oxygen saturation. Two important fetal physiological parameters, i.e., the fetal heart rate and the fetal blood oxygen saturation, can be provided to the medical personnel at the same time, which has great practical significance for the fetus, pregnant women and society. The present invention is a new invention that is further produced in the process of developing a specific product according to the above patent. The applicant found that, because of the great uncertainty of the positions (fetal positions) of the fetus in the mother's uterus, the fetal positions of different pregnant women were different, the fetal positions of the same pregnant woman at different pregnancy stages varied greatly, the postures of the fetus in the uterus also varied at any time, and therefore the fetal blood oxygen saturations of different parts were also different. Therefore, when a photoelectric sensor of the fetal SpO2 detection system of the Chinese patent (ZL201310182965.2) is applied to a specific part outside the abdominal cavity of the pregnant woman, a photoelectrical signal related to the fetal SpO2, which is sensed by the photoelectrical sensor, has great uncertainty. This uncertainty directly affects the specificity of the detection result. That is, when the detection result shows positive (lower blood oxygen saturation), the actual SpO2 of the fetus is normal. As a result of this case, unnecessary human intervention and even surgical intervention will be caused possibly. These interventions will lead to an increase in medical costs and medical risks, as well as an increase in maternal and child suffering. It can thus be seen that a real problem faced by the trans-abdominal non-invasive detection of the fetal blood oxygen saturation is: how to solve the problem of the influences of the uncertainty of the fetal position on the detection result. A further problem is the attenuation of light. An optical signal received by a light receiver must be the light of a specific wavelength, which is irradiated from the outside of the abdominal cavity of the pregnant woman to the fetus in the abdominal cavity and then returned from the fetus to the outside of the abdominal cavity of the pregnant woman through the abdominal cavity of the pregnant woman. It takes a long optical path from emission to reception, and the light attenuation is directly proportional to the square of the optical path. In addition, the optical signal received by the light receiver, which is related to the fetal blood oxygen saturation, is extremely weak light obtained after undergoing complex processes such as absorption, reflection and scattering of fetal tissues and pregnant women tissues (skin, fat, uterus, amniotic fluid, etc). The light is weak enough to threaten the successful detection and the practicability of trans-abdominal non-invasive detection of fetal blood oxygen saturation. Therefore, it is necessary for the trans-abdominal non-invasive blood oxygen saturation detection device to solve the problem of the intensity of fetal blood flow-related signals received by a light receiving device, as well as the problem of signal interference, to improve the signal intensity to eliminate noise interference, and to increase the signal to noise ratio. Therefore, in order to develop a successful trans-abdominal non-invasive fetal blood oxygen saturation detection device, it is necessary to solve the above two problems at the same time, and hence illumination and the intensity of the fetal blood flow-related signals received by the light receiver become the keys to solve the two problems.

The applicant also found in studies that the trans-abdominal non-invasive fetal blood oxygen saturation monitoring system must allow light of sufficient power to irradiate the abdomen of the pregnant woman to ensure that the light receiver received an effective fetal-related optical signal. However, if the luminous power of a light source is increased blindly, a possibility that the pregnant woman feels uncomfortable or is burned on the skin during use will be caused because a currently used light-emitting element (such as LED or laser) has a small light-emitting area and is usually clung to the skin of the pregnant woman. According to a document issued by the International Commission of Nob-Ionizing Radiation Protection (ICNIRP) in 2000, a light wave with a wavelength in the range of 400 nm to 1400 nm will burn the skin if a few milliwatts of optical power last for 100 seconds. Therefore, in order to improve the practicability and comfort of the detection device, it is very necessary to eliminate the risk of optical radiation damage caused by local burns.

SUMMARY OF THE INVENTION

An objective of the present invention is to provide a trans-abdominal non-invasive blood oxygen saturation detection device, which can improve the intensity of a received optical signal related to the fetal blood oxygen saturation.

In order to achieve the said objective, the present invention adopts the following technical solution:

a trans-abdominal non-invasive fetal blood oxygen saturation detection device comprises a trans-abdominal fetal oximeter and a signal detection assembly connected to the trans-abdominal fetal oximeter; the trans-abdominal oximeter comprises a signal processing controller; the signal detection assembly comprises a light-emitting light source device, a light receiving device for collecting an optical signal related to fetal blood oxygen saturation from the outside of the abdominal cavity of a pregnant woman, and a reference signal detection device for collecting one or more of a fetal heart rate signal, a pregnant woman heart rate signal and a pregnant woman pulse blood oxygen saturation optical signal; the light-emitting light source device, the light receiving device and the reference signal detection device are all connected to the signal processing controller;

the light-emitting light source device is configured to irradiate two or more different wavelengths of light into the abdominal cavity of the pregnant woman;

the light receiving device comprises a plurality of light receivers respectively placed at a plurality of different positions outside the abdominal cavity of the pregnant woman and is configured to collect a plurality of optical signals related to the fetal blood oxygen saturation, which are scattered and reflected back from the abdominal cavity of the pregnant woman through the plurality of light receivers, synthesize an optical signal sum related to the fetal blood oxygen saturation and then output the optical signal sum to the signal processing controller;

the signal processing controller is configured to calculate the fetal blood oxygen saturation according to the optical signal sum outputted by the light receiving device, and according to any one or more of the fetal heart rate signal, the pregnant woman heart rate signal and the pregnant woman pulse blood oxygen saturation optical signal which are collected from the reference signal detection device.

Preferably, the light receiving device comprises a plurality of light receivers and an adder connected to the plurality of light receiver, wherein the adder is connected to the signal processing controller of the trans-abdominal fetal oximeter.

Preferably, the light receiving device comprises a plurality of light receivers and a primary signal processor connected to the plurality of light receivers, wherein the primary signal processor comprises an interface for receiving the fetal heart rate signal, and is configured to synthesize the plurality of received optical signals related to the fetal blood oxygen saturation into an optical signal sum through the following steps:

step A: performing correlation analysis on the plurality of received optical signals related to the fetal blood oxygen saturation and the fetal heart rate signals respectively to obtain correlation coefficients of the respective optical signals;

step B: obtaining corresponding weighting coefficients of the optical signals based on the correlation coefficients; and step C: superimposing the plurality of optical signals according to the respective weighting coefficients to obtain an optical signal sum related to the fetal blood oxygen saturation.

Preferably, the step B comprises: setting the weighting coefficient as 0 if the correlation coefficient of each optical signal is less than a preset correlation threshold; obtaining the weighting coefficient according to the correlation coefficient if the correlation coefficient is higher than the preset correlation threshold, and superimposing the plurality of optical signals according to the respective weighting coefficients to obtain the optical signal sum.

Preferably, the step A comprises: performing correlation analysis on each received optical signal related to the fetal blood oxygen saturation and the received fetal heart rate signal in a time domain to obtain the correlation coefficient of each optical signal.

Preferably, the step A comprises: transmitting each received optical signal related to the fetal blood oxygen saturation from the time domain to a frequency domain to obtain an optical signal spectrum, and meanwhile transmitting the received fetal heart rate signal from the time domain to the frequency domain to obtain a fetal frequency domain optical power spectrum; and performing correlation analysis on the optical signal spectrum and the fetal frequency domain optical power spectrum in the frequency domain to obtain the correlation coefficient of each optical signal.

Preferably, the step A further comprises: filtering out a signal spectrum power other than the fetal spectrum power from the optical signal spectrum to obtain a filtered optical signal spectrum, and restoring the filtered optical signal spectrum from the frequency domain back to the time domain to obtain a filtered optical signal as a weighted superimposed optical signal.

Preferably, the primary signal processor comprises a plurality of signal analyzers and an addition selector connected to the plurality of signal analyzers, wherein a plurality of signal analyzers is configured to analyze correlation coefficients of the optical signals related to the fetal blood oxygen saturation, which are collected by the plurality of light receivers, and the fetal heart rate signals respectively, and the additional selector is configured to superimpose the weights of a plurality of digital signals to synthesize an optical signal sum according to the analysis results from the signal analyzers.

Preferably, the primary signal processor is a single chip microcomputer.

Preferably, the detection device comprises a fetal blood oxygen optical signal collection device integrated with the light-emitting light source device and the light receiving device, wherein the fetal blood oxygen optical signal collection device comprises a photosensor mounting mechanism on which the light-emitting light source device and the light receiving device comprising a plurality of light receivers are integrally mounted.

Preferably, the plurality of light receivers of the light receiving device is placed around a light-emitting light source of the light-emitting light source device to form a circular shape.

Preferably, the plurality of light receivers of the light receiving device is placed around the light-emitting light source of the light-emitting light source device to form a square shape; or the plurality of light receivers of the light receiving device forms an array of i rows*j columns and is placed on one side of the light-emitting light source of the light-emitting light source device, both i and j being integers greater than 0; or the plurality of light receivers of the light receiving device forms two arrays of i rows*j columns and is placed on two sides of the light-emitting light source of the light-emitting light source device respectively, both i and j being integers greater than 0.

Preferably, the fetal blood oxygen optical signal collection device further comprises a conduction switch controlled by a signal generated by a pulse timing sequence emitted by the light-emitting light source device, wherein an optical signal received by each of the light receivers of the light receiving device is converted into an electrical signal which is then passed through the conduction switch, such that the illumination of the light-emitting light source device and the received optical signal passed through the conduction switch are synchronized, and only the optical signal synchronized with the illumination of the light-emitting light source device within a narrow pulse time can be transmitted to an analog-to-digital converter of the light receiving device and converted into a digital signal for further processing.

Preferably, the light-emitting light source device comprises a light-emitting light source and a light source driver connected to the light-emitting light source, wherein the light source driver is connected to the signal processing controller, and the light source driver is configured to drive the light-emitting light source to emit pulsed light having a frequency higher than 20 Hz under the control of the signal processing controller, a duty ratio of the pulse of the pulsed light being less than 40%.

Preferably, the light-emitting light source device comprises an light-emitting light source comprising a plurality of first light-emitting units and a plurality of second light-emitting units, wherein each of the plurality of first light-emitting units is capable of emitting red or infrared light of a first wavelength, and each of the plurality of second light-emitting units is capable of emitting red or infrared light of a second wavelength, the first wavelength being different from the second wavelength; the number of the first light-emitting units is the same as that of the second light-emitting units; the plurality of first light-emitting units and the plurality of second light-emitting units are arranged in a row and column light source array.

Preferably, the plurality of first light-emitting units is placed at equal or unequal intervals to form a m*n first row and column light source array, and the plurality of second light-emitting units is placed at equal or unequal intervals to form a m*n second row and column light source array, wherein n is an integer greater than 1, and m is an integer greater than or equal to 1.

Preferably, the plurality of first light-emitting units and the plurality of second light-emitting unit are placed at equal or unequal intervals to form a row and column light source array of m rows and 2*n columns, wherein each column of the row and column light source array is a first light-emitting unit column composed of the first light-emitting units or a second light-emitting unit column composed of the second light-emitting units, and the first light-emitting unit columns and the second light-emitting unit columns are alternately arranged, wherein n is an integer greater than 1, and m is an integer greater than or equal to 1;

or, the plurality of first light-emitting units and the plurality of second light-emitting unit are placed at equal or unequal intervals to form a row and column light source array of 2*m rows and n columns, wherein each row of the row and column light source array is a first light-emitting unit row composed of the first light-emitting units or a second light-emitting unit row composed of the second light-emitting units, and the first light-emitting unit rows and the second light-emitting unit rows are alternately arranged, wherein n is an integer greater than or equal to 1, and m is an integer greater than 1.

Preferably, in the row and line light source array composed of the plurality of first light-emitting units and the plurality of second light-emitting units, the first light-emitting units and the second light-emitting units are alternately arranged such that the first light-emitting units and the second light-emitting units in each row of the row and column light source array are alternately arranged, and the first light-emitting units and the second light-emitting units in each column of the row and column light source array are also alternately arranged.

Preferably, a light diffusion lens having a diffused irradiation area is arranged outside the row and column light source array composed of the plurality of first light-emitting units and the plurality of second light-emitting units of the light-emitting light source.

The light receiving device of the trans-abdominal non-invasive fetal blood oxygen saturation detection device of the present invention collects a plurality of optical signals related to the fetal blood oxygen saturation through a plurality of light receivers 204 and synthesizes the same into an optical signal sum to improve the intensity of the received optical signals.

As a preferred solution, the light receiving device 91 is implemented by the plurality of light receivers 204 and the adder with a simple structure and low cost, without improving the existing trans-abdominal fetal oximeter.

As a preferred solution, the plurality of light receivers 204 collects a plurality of optical signals related to the fetal blood oxygen saturation, superimposes and synthesizes the same into an optical signal sum to improve the intensity of the received optical signals, performs correlation analysis on the optical signals collected by the plurality of light receivers 204 and the fetal heart rate signals collected at the same time, and then weights and superimposes the same to reduce the noise signal interference unrelated to the fetal blood oxygen saturation in the light sources, such that the signal to noise ratio of the collected optical signals is increased to improve the detection accuracy and reliability of the trans-abdominal fetal blood oxygen saturation detection device. In particular, when the plurality of received optical signals related to the fetal blood oxygen saturation is subjected to the correlation analysis with the fetal heart rate signals respectively, the signals are transmitted from the time domain to the frequency domain for correlation analysis, and a signal spectrum power other than the fetal spectrum power is filtered out from the optical signal spectrum, such that the noise interference is greatly reduced, and the intensity of the optical signals related to the fetal blood oxygen saturation is improved.

In addition, by means of reasonable layout of a plurality of light receivers 204 of the light receiving device 91 and the light-emitting light source device 92, if the plurality of light receivers 204 is arranged around the light-emitting light source device 92 in a circular shape, the light source can be reasonably utilized to improve the intensity of the signals collected by the light receiving device 91. The light-emitting light source device adopts a plurality of first light-emitting units and a plurality of second light-emitting units, and the plurality of first light-emitting units and the plurality of second light-emitting units are placed in an equidistant row and column light source array to realize a wide range of multiple paths to increase the luminous power of the light source. At the same time, illumination does not happen in a point, such that the received optical signals related to the fetal blood oxygen saturation are greatly intensified than that in the original device, but the optical power received by the abdominal skin per unit area of a pregnant woman is low or not increased.

DETAILED DESCRIPTION OF THE PREFERRED EMBODIMENTS

Specific embodiments of a trans-abdominal non-invasive fetal blood oxygen saturation detection device of the present invention will be further described with reference to the embodiments given in FIGS. 1 to 21 below.

Figure 1:
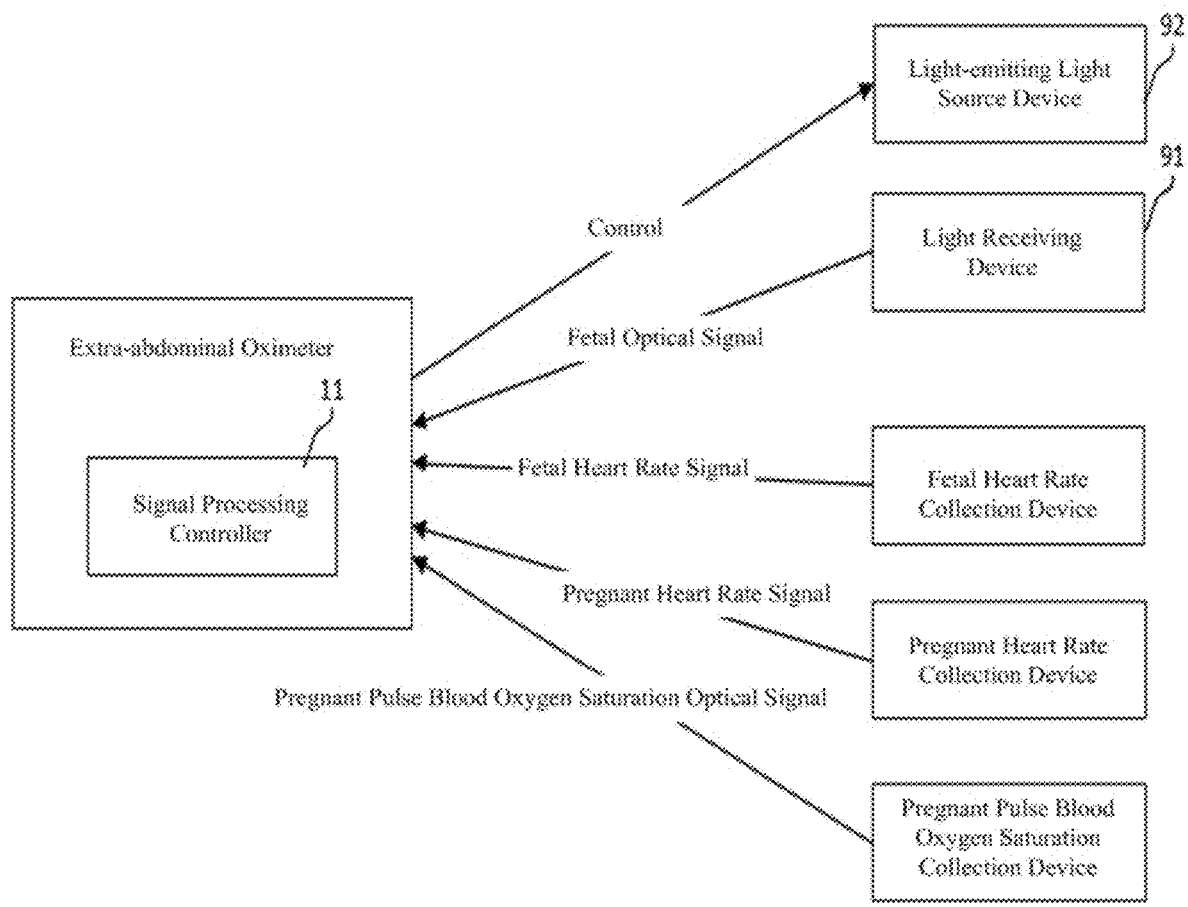
FIG. 1 is a structural block diagram of a trans-abdominal non-invasive fetal blood oxygen saturation detection device of the present invention.

As shown in FIG. 1, the present invention relates to a trans-abdominal non-invasive fetal blood oxygen saturation detection device which generally comprises a trans-abdominal fetal oximeter and a signal detection assembly connected to the trans-abdominal fetal oximeter. The trans-abdominal oximeter comprises a signal processing controller 11. The signal detection assembly comprises a light-emitting light source device 92 for irradiating two or more different wavelengths of light into the abdominal cavity of a pregnant woman, a light receiving device 91 for collecting an optical signal related to the fetal blood oxygen saturation collected from the outside of the abdominal cavity of the pregnant woman, and a reference signal detection device for collecting one or more of a fetal heart rate signal, a pregnant woman heart rate signal and a pregnant woman pulse blood oxygen saturation optical signal. The reference signal detection device comprises a fetal heart rate collection device for collecting a fetal heart rate signal from the outside of the abdominal cavity of the pregnant woman, and/or a pregnant woman heart rate collection device for collecting a pregnant woman heart rate signal, and/or a pregnant woman pulse blood oxygen saturation collection device for collecting a pregnant woman pulse blood oxygen saturation optical signal. The light receiving device 91, the light-emitting light source device 92, the fetal heart rate collection device, the pregnant woman heart rate collection device and the pregnant woman pulse blood oxygen saturation collection device are all connected to the signal processing controller 11. The signal processing controller 11 is configured to calculate the fetal blood oxygen saturation according to the collected optical signal related to the fetal blood oxygen saturation, and based on any one or more of the fetal heart rate signal, the pregnant woman heart rate signal, and the pregnant woman pulse blood oxygen saturation optical signal.

The present invention relates to a technology for detecting a blood oxygen saturation of a blood stream of a fetus outside the body of a pregnant woman. This technology creatively realizes trans-abdominal non-invasive fetal blood oxygen saturation detection, without any operation of going deep into the abdominal cavity of the pregnant woman during the detection process and without a need of applying a photoelectric sensor to a specific position of the fetus. A specific solution including the problem of how to convert processing signals has been disclosed in the inventor's earlier invention patent CN201310182965.2, and will not be described again.

Figure 2:
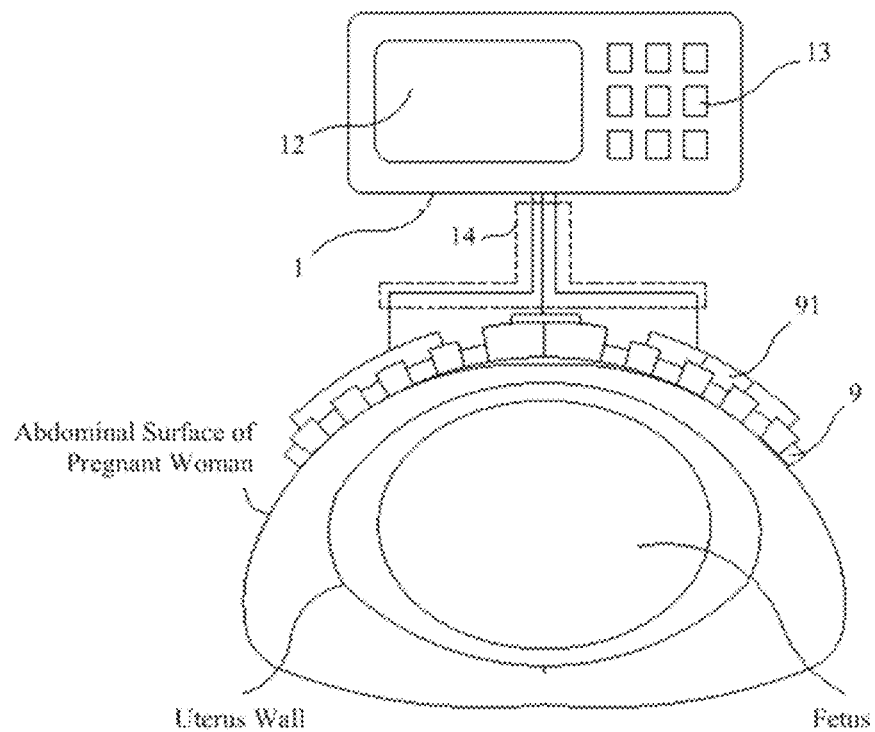
FIG. 2 is a structural schematic diagram of a trans-abdominal non-invasive fetal blood oxygen saturation detection device of the present invention.
Figure 3:
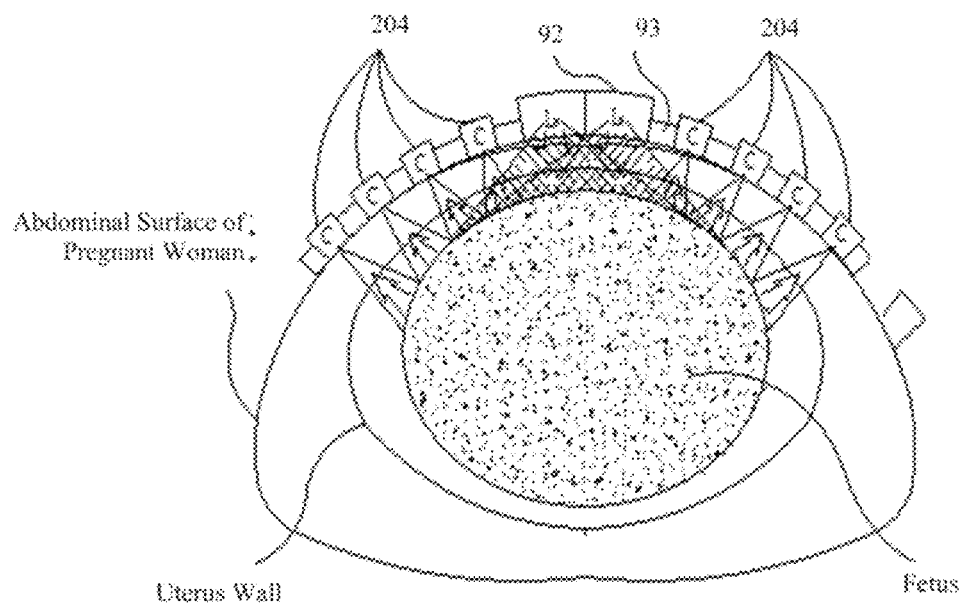
FIG. 3 is a structural schematic diagram of a fetal blood oxygen optical signal collection device of the present invention.

As shown in FIGS. 2-3, one embodiment of an trans-abdominal non-invasive fetal blood oxygen saturation detection device of the present invention comprises an trans-abdominal fetal oximeter and a fetal blood oxygen optical signal collection device 9 connected to the trans-abdominal fetal oximeter. The trans-abdominal fetal oximeter comprises a signal processing controller 11, and a display module 12 and an operation module 13 which are connected to the signal processing controller 11. The fetal blood oxygen optical signal collection device 9 comprises a photosensor mounting mechanism 93 on which a light-emitting light source device 92 and a light receiving device 91 comprising a plurality of light receivers 204 are integrally mounted. The light-emitting light source device 92 and the light receiving device 91 are integrated together to form a collection device for collecting a fetal blood oxygen optical signal. The fetal blood oxygen optical signal collection device 9 can tightly wrap the light-emitting light source device 92 and the light receiving device 91 onto the abdominal body surface of the pregnant woman in an appressed manner, and can be adjusted according to a fetus moving position. Preferably, the fetal blood oxygen optical signal collection device 9 is a soft member on which the light-emitting light source device 92 and the light receiving device 91 comprising the plurality of light receivers 204 can be fixedly mounted and which can be fixed on the abdomen of the pregnant woman and wrapped to the abdomen of the pregnant woman. For example, the photosensor mounting mechanism 93 of the fetal blood oxygen optical signal collection device 9 may be a waistband attached to the abdomen of the pregnant woman, a wearable abdominal scarf, a dudou or other device on which the light-emitting light source device 92 and the light receiving device 91 comprising the plurality of light receivers 204 can be mounted and which can be fixed to the abdomen of the pregnant woman. The fetal blood oxygen optical signal collection device 9 is connected to the abdominal fetal oximeter via a communication link 14. The communication link 14 may be a wired link or a wireless link. The wireless link may use WIFI, Bluetooth and other wireless communication protocols. The display module 12 may be an LED screen, an LCD screen or a touch screen. The operation module 13 may be a keyboard.

Further, the trans-abdominal non-invasive fetal blood oxygen saturation detection device further comprises a fetal heart rate collection device (not shown). The fetal blood oxygen optical signal collection device 9 and the fetal heart rate collection device are combined together to form an trans-abdominal fetal blood oxygen probe, or the fetal heart collection device is also integrated on the photosensor mounting mechanism 93 of the fetal blood oxygen optical signal collection device 9 to form a trans-abdominal fetal blood oxygen probe for acquiring various signals required by the trans-abdominal fetal oximeter. The trans-abdominal fetal blood oxygen probe is connected to the trans-abdominal fetal oximeter 1 via the communication link 14. For example, in one embodiment, the fetal blood oxygen optical signal collection device 9 and the fetal heart rate collection device are of two independent collection devices which together form the trans-abdominal fetal blood oxygen probe. The fetal blood oxygen optical signal collection device 9 and the fetal heart rate collection device are respectively connected to the trans-abdominal fetal oximeter 1. The trans-abdominal fetal oximeter 1 is provided with an optical signal interface connected to the light receiving device 91, a light-emitting light source interface connected to the light-emitting light source device 92, and a fetal heart rate detection interface connected to the fetal heart rate collection device. The light-emitting light source device 92, the light receiving device 91 and the fetal heart rate collection device are respectively connected to the optical signal interface, the light-emitting light source interface and the fetal heart rate detection interface respectively via an optical signal link, a light-emitting light source link and a fetal heart rate signal link. The optical signal link, the light-emitting light source link and the fetal heart rate signal link may be a wired link or a wireless link respectively, and the wireless link may use WIFI, Bluetooth, and other wireless communication protocols. For example, in another embodiment, the light-emitting light source device 92 and the light receiving device 91 of the fetal blood oxygen optical signal collection device 9, and the fetal heart rate collection device are integrated on the photosensor mounting mechanism 93 to form the trans-abdominal fetal blood oxygen probe. The trans-abdominal fetal oximeter 1 is provided with a first wireless transmitter/receiver. The optical signal interface, the light-emitting light source interface and the fetal heart rate detection interface of the trans-abdominal oximeter 1 are connected to the first wireless transmitter/receiver respectively. The optical sensor mounting mechanism 93 is provided with a second wireless transmitter/receiver. The light-emitting light source device 92, the light receiving device 91 and the fetal heart rate collection device are respectively connected to the second wireless transmitter/receiver, and are connected to the trans-abdominal fetal oximeter 1 via links of the second wireless transmitter/receiver and the first wireless transmitter/receiver. Further, the trans-abdominal fetal blood oxygen probe may further comprise a pregnant woman heart rate collection device and/or a pregnant woman pulse blood oxygen saturation collection device (not shown).

As one improvement of the present invention, the signal processing controller 11 controls the light-emitting light source device 92 to irradiate two or more different wavelengths of light into the abdominal cavity of a pregnant woman. The light receiving device 91 comprises a plurality of light receivers 204 respectively placed at a plurality of different positions outside the abdominal cavity of the pregnant woman. The light receiving device 91 collects, by the plurality of light receivers 204, a plurality of optical signals related to fetal blood oxygen saturation, which are scattered and reflected back from the abdominal cavity of the pregnant woman, and superimposes the optical signals into an optical signal sum related to the fetal blood oxygen saturation and outputs it to the signal processing controller 11. The light receiving device 91 of the present invention comprises a plurality of light receivers 204 respectively placed at a plurality of different positions outside the abdominal cavity of the pregnant woman, and is configured to collect a plurality of optical signals related to the fetal blood oxygen saturation, which are returned from the abdominal cavity of the pregnant woman, superimpose and summarize the optical signals into an optical signal sum and then transmit the optical signal sum to the signal processing controller 11. The signal processing controller 11 is configured to calculate the fetal blood oxygen saturation according to the optical signal sum outputted by the light receiving device 91, and according to any one or more of a fetal heart rate signal, a pregnant woman heart rate signal and a pregnant woman pulse blood oxygen saturation optical signal which are collected from the reference signal detection device. The light receiving device 91 of the present invention is configured to collect, via the plurality of light receivers 204, a plurality of optical signals related to the fetal blood oxygen saturation, then superimpose and summarize the collected optical signals and then transmit the optical signal sum to the signal processing controller 11, such that the intensity o the optical signals related to the blood stream of the fetus among the received signals is effectively improved. Each of the light receivers 204 is a silicon photodiode, an avalanche photodiode, a photomultiplier tube or other photoelectric conversion device. The light-emitting light source device 92 includes at least two light sources of different wavelengths, which may be red light at 500 nm to infrared light at 1000 nm, preferably 660 nm, 740 nm, 880 nm, 940 nm. The light-emitting light source is an LED or a laser or other light-emitting light source.

Figure 4:
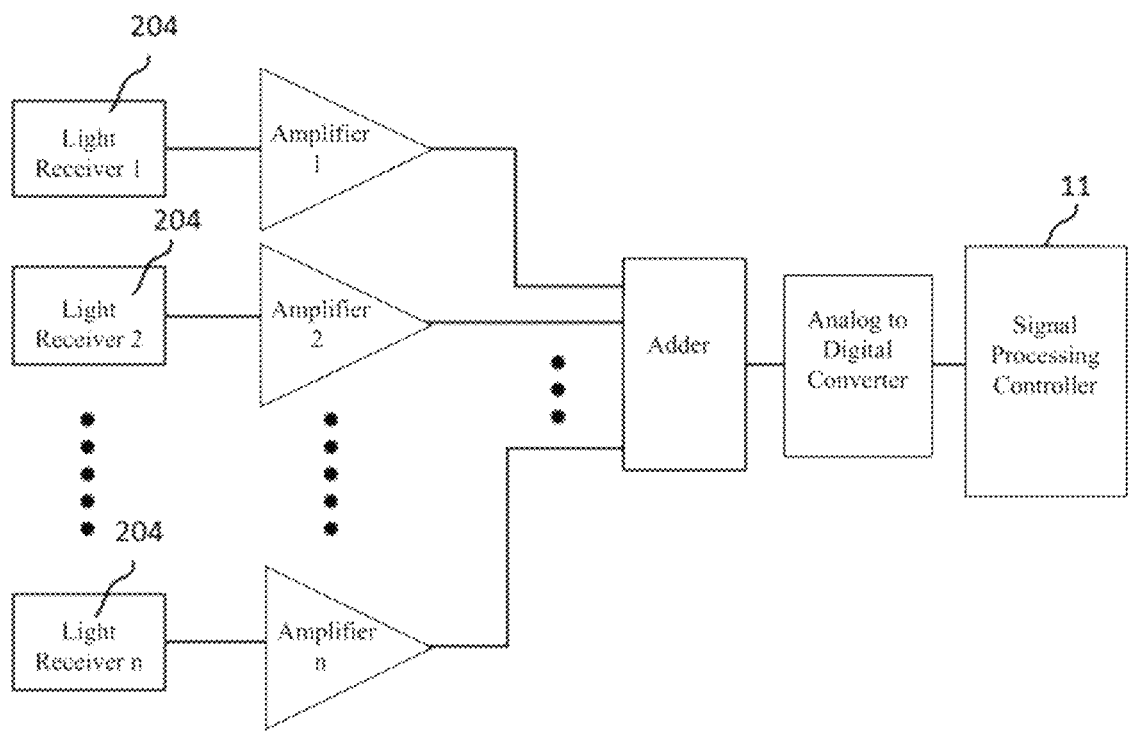
FIGS. 4-5 are structural drawings of two embodiments of a light receiving device of the present invention.
Figure 5:
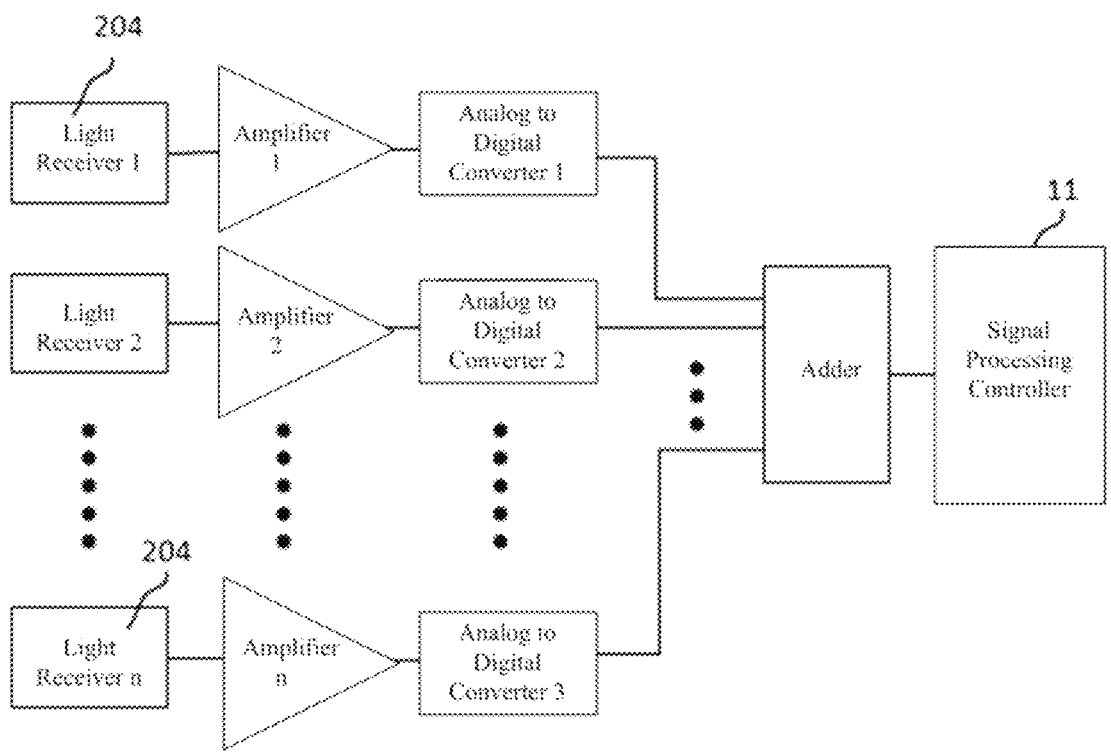

As shown in FIGS. 4-5, the light receiving device 91 comprises a plurality of light receivers 204 and an adder connected to the plurality of light receiver 204, wherein the adder is connected to the signal processing controller 11 of the trans-abdominal fetal oximeter. Each of the light receivers 204 is configured to receive optical signals related to fetal blood oxygen saturation returned from the abdominal cavity of the pregnant woman, and convert the optical signals into a plurality of electrical signals. The adder is configured to superimpose the plurality of electrical signals and output an optical signal sum related to the fetal blood oxygen saturation to the signal processing controller 11. The light receiving device 91 is realized by the plurality of light receivers 204 and the adder with a simple structure and low cost, without improving the existing trans-abdominal fetal oximeter.

As shown in FIG. 4, in an embodiment of the light receiving device 91 of the present invention, the light receiving device 91 comprises a plurality of light receivers 204, and a plurality of amplifiers connected to the plurality of light receivers 204 respectively. The plurality of amplifiers is connected to the adder. The adder is connected to the signal processing controller 11 of the trans-abdominal fetal oximeter via a digital-to-analog converter. Each of the light receivers 204 is configured to receive optical signals related to fetal blood oxygen saturation returned from the abdominal cavity of the pregnant woman, and convert the optical signals into a plurality of electrical signals. The plurality of electrical signals are amplified by the amplifiers and superimposed by the adder, and then converted into an optical signal sum of digital signals by the digital-to-analog converters, which is then output to the signal processing controller 11.

As shown in FIG. 5, in another embodiment of the light receiving device 91 of the present invention, the light receiving device 91 comprises a plurality of light receivers 204, a plurality of amplifiers connected to the plurality of light receivers 204 respectively and a plurality of digital-to-analog converters connected to the plurality of amplifiers respectively. The plurality of digital-to-analog converters is connected to the adder. The adder is connected to the signal processing controller 11 of the trans-abdominal fetal oximeter. Each light receiver 204 converts the optical signals into a plurality of electrical signals, the electrical signals are respectively amplified by the amplifiers and converted into digital signals through the digital-to-analog converters, and the digital signals are then superimposed into an optical signal sum by the adder and output to the signal processing controller 11.

As an improvement of the present invention, the fetal blood oxygen optical signal collection device 9 integrates the light-emitting light source device 92 and the light receiving device 91 comprising the plurality of light receivers 204, which not only makes it convenient to use, but also causes the previous layout of the light-emitting light source device 92 and the plurality of light receivers 204 to be more reasonable, and the paths for collecting scattering and reflection to be closer, such that the light source can be reasonably utilized to improve the intensity of the signals collected by the light receiving device 91.

Figure 6:
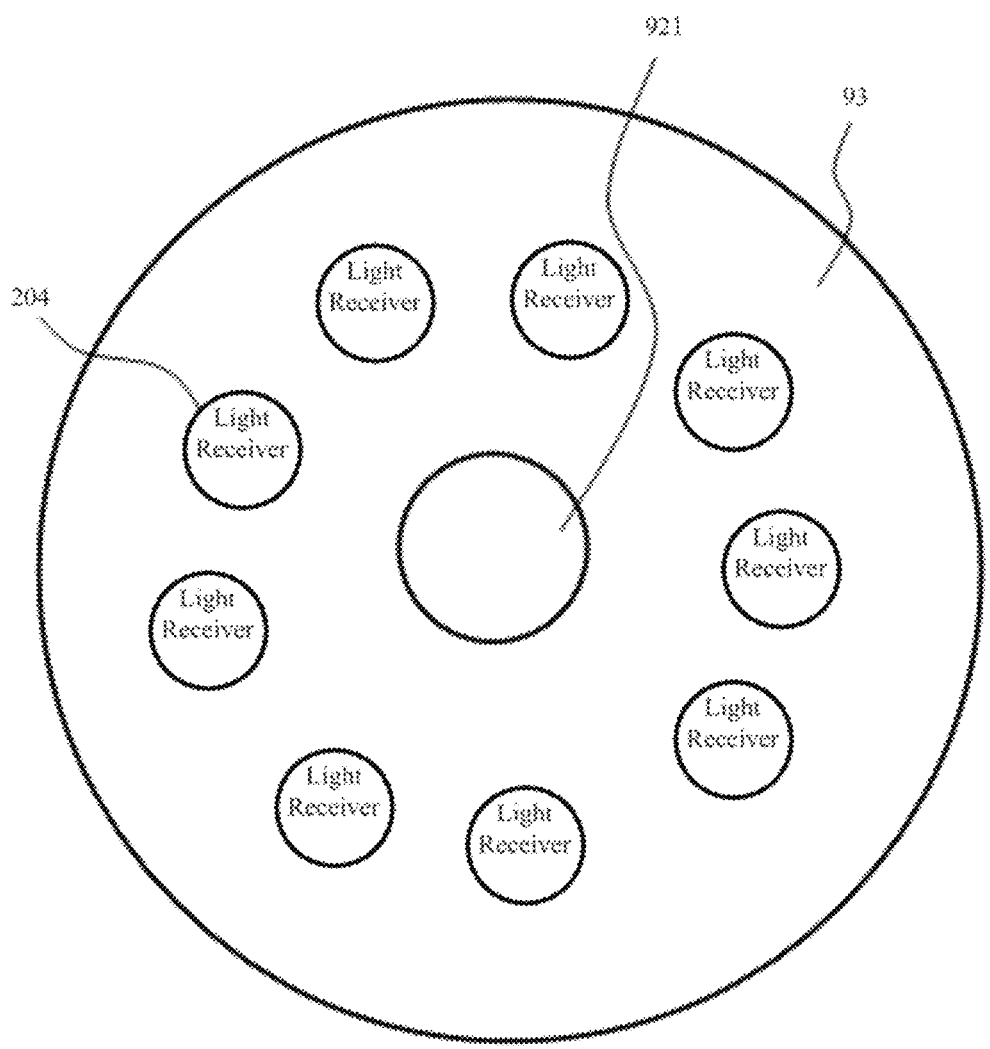
FIGS. 6-11 are structural drawings of six embodiments in terms of a layout structure of a plurality of light receivers and the light-emitting light source of the fetal blood oxygen optical signal collection device of the present invention.

As shown in FIG. 6, in a preferred embodiment of the fetal blood oxygen optical signal collection device 9 of the present invention, the plurality of light receivers 204 of the light receiving device 91 and the light-emitting light source device 92 are mounted on the sensor mounting mechanism 93. The plurality of light receivers 204 of the light receiving device 91 is arranged around a light-emitting light source 921 of the light-emitting light source device 92 to form a circular shape. Preferably, the photosensor mounting mechanism 93 is capable of being buckled on the abdomen of the pregnant woman in a dome shape. The light-emitting light source of the light-emitting light source device 92 is located in the middle of the dome, i.e., in the middle of the top side of the abdomen of the pregnant woman. The plurality of light receivers 204 of the light receiving device 91 is arranged around the side surface of the abdomen of the pregnant woman to form a circular shape. The light-emitting light source and the plurality of light receivers 204 form a dome shape. By means of reasonable layout of the plurality of light receivers 204 of the light receiving device 91 and the light-emitting light source 921 of the light-emitting light source device 92, the light source can be reasonably utilized to improve the intensity of the signals collected by the light receiving device 91.

Figure 7:
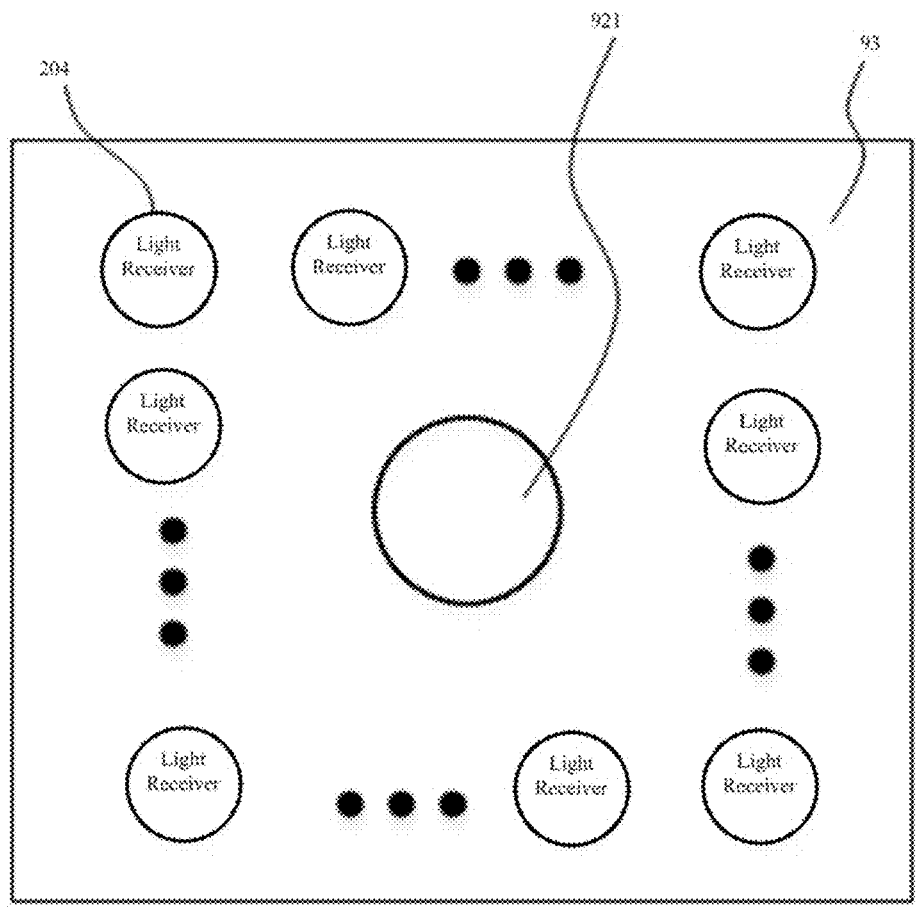
Figure 8:
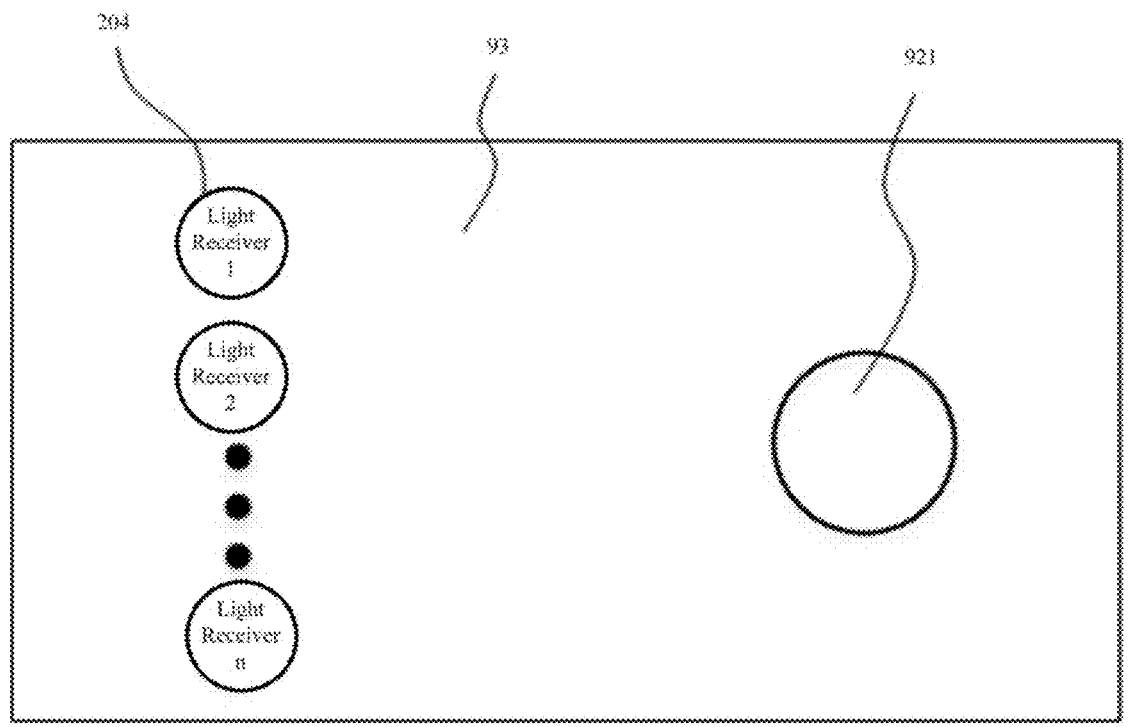
Figure 9:
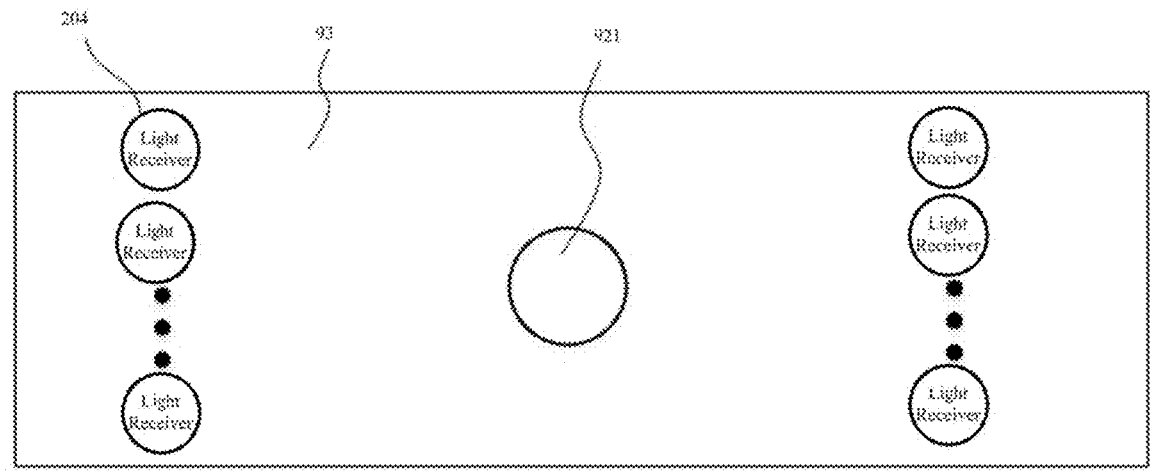
Figure 10:
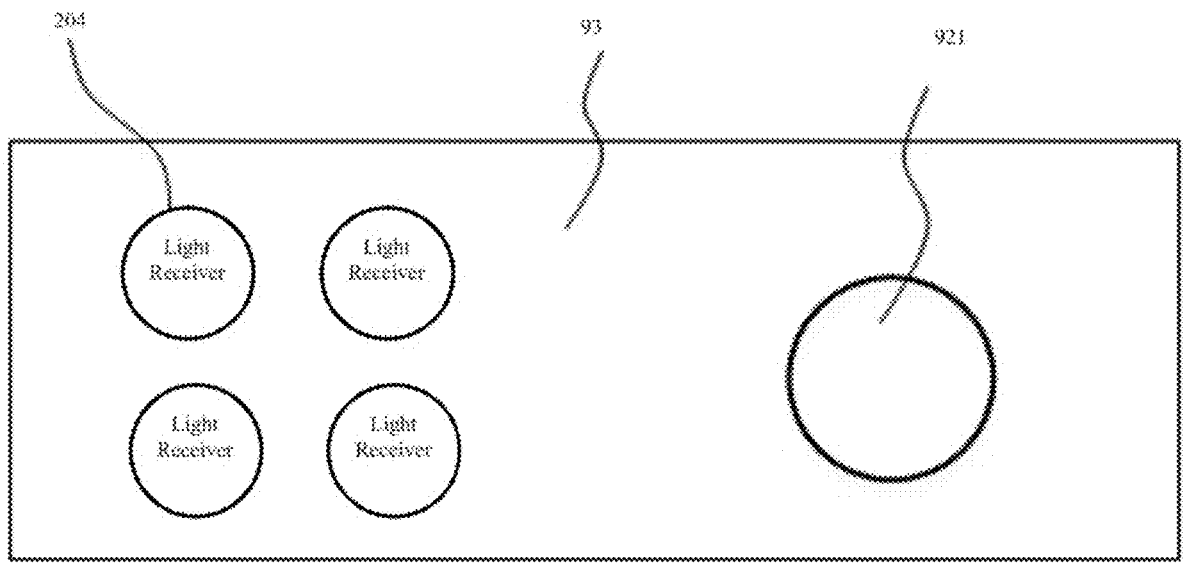
Figure 11:
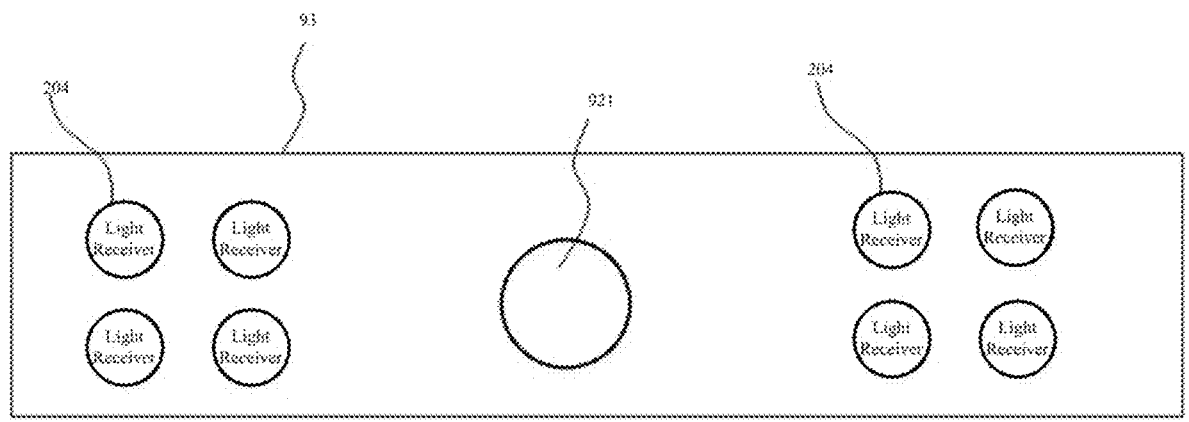

As shown in FIG. 7, in a preferred embodiment of the fetal blood oxygen optical signal collection device 9 of the present invention, the plurality of light receivers 204 of the light receiving device 91 is arranged around the light-emitting light source 921 of the light-emitting light source device 92 to form a square shape.

In several embodiments as shown in FIGS. 8 to 11, the plurality of light receivers 204 of the light receiving device 91 form an array of i rows*j columns and is placed on one side of the light-emitting light source 921 of the light-emitting light source device 92, both i and j being integers greater than 0; or the plurality of light receivers 204 of the light receiving device 91 form two arrays of i rows*j columns and is placed on two side of the light-emitting light source 921 of the light-emitting light source device 92 respectively, both i and j being integers greater than 0.

Further, in another embodiment of the fetal blood oxygen optical signal collection device 9 of the present invention, the fetal blood oxygen optical signal collection device 9 further comprises a conduction switch controlled by a signal generated by a pulse timing sequence emitted by the light-emitting light source device 92. An optical signal received by each of the light receivers 204 of the light receiving device 91 is converted into an electrical signal and then passed through the conduction switch, such that the illumination of the light-emitting light source device 92 and the received optical signal passed through the conduction switch are synchronized, and only the optical signal synchronized with the illumination of the light-emitting light source device 92 within a narrow pulse time can be transmitted to the analog-to-digital converter of the light receiving device 91 and converted into a digital signal for further processing.

As an improvement of the present invention, the light-emitting light source device 92 of the present invention comprises a light-emitting light source 921 and a light source driver connected to the light-emitting light source 921. The light source driver is connected to the signal processing controller, and is configured to drive the light-emitting light source 921 to emit pulsed light having a frequency higher than 20 Hz under the control of the signal processing controller, a duty ratio of the pulse of the pulsed light being less than 40%. Preferably, the pulsed light has a frequency in the range of 400 Hz to 5000 Hz, but not including frequencies of 50 Hz, 60 Hz, and integer multiples thereof. The light-emitting light source device 92 of the present invention adopts a pulsed optical signal with a relatively small duty ratio, such that the average optical power received by the human body is much less than the instantaneous maximum luminous power, thereby ensuring the human body safety, and solving the problem that excessive luminous power may cause damage to the pregnant women and fetus while improving the intensity of the signals. The light source driver in the present embodiment may be used for the light-emitting light source 921 having a single first light-emitting unit and a single second light-emitting unit, or may also be used for the light-emitting light source 921 having a plurality of first light-emitting units and a plurality of second light-emitting units.

As an improvement of the present invention, the light-emitting light source device of the present invention comprises a light-emitting light source 921 comprising a plurality of first light-emitting units and a plurality of second light-emitting units, and a light source driver connected to the light-emitting light source 921. Each of the plurality of first light-emitting units is capable of emitting red or infrared light of a first wavelength, and each of the plurality of second light-emitting units is capable of emitting red or infrared light of a second wavelength, the first wavelength being different from the second wavelength. The number of the first light-emitting units is the same as that of the second light-emitting units. The plurality of first light-emitting units and the plurality of second light-emitting units are placed in a row and column light source array. The plurality of first light-emitting units and the plurality of second light-emitting units are alternately lighted up under the control of the light source driver. The plurality of first light-emitting units and the plurality of second light-emitting units in the row and column light source array may be arranged at equal or unequal intervals, and preferably, the distance between every two of the light-emitting units in the row and column light source array is equal. The light-emitting light source device 92 of the present invention adopts a plurality of first light-emitting units and a plurality of second light-emitting units, and the plurality of first light-emitting units and the plurality of second light-emitting units are placed in an equidistant row and column light source array to realize a wide range of multiple paths to increase the luminous power of the light source. At the same time, illumination does not happen in a point, such that the received optical signals related to the fetal oxygen saturation are greatly intensified than that in the original device, but the optical power received by the abdominal skin per unit area of a pregnant woman is low or not increased. Preferably, the light-emitting light source device 92 comprises at least two first light-emitting units and at least two second light-emitting units. The first light-emitting units and the second light-emitting units may be LEDs capable of emitting red or infrared light, lasers or other light sources, preferably LEDs capable of emitting red light at 600 nm to infrared light at 950 nm. If the first wavelength is from red light, the second wavelength is from infrared light; and if the first wavelength is from infrared light, the second wavelength is from red light. Preferably, the first wavelengths of the red or infrared light emitted by the plurality of first light-emitting units are exactly the same, which, however, is practically difficult to achieve, and therefore, the first wavelengths of the red or infrared light emitted by the plurality of first light-emitting units are substantially the same, and within a small deviation range, all of which fall within the protection scope of the present application. In the same way, the second wavelengths of red or infrared light emitted by the plurality of second light-emitting units are also similar.

Figure 12:
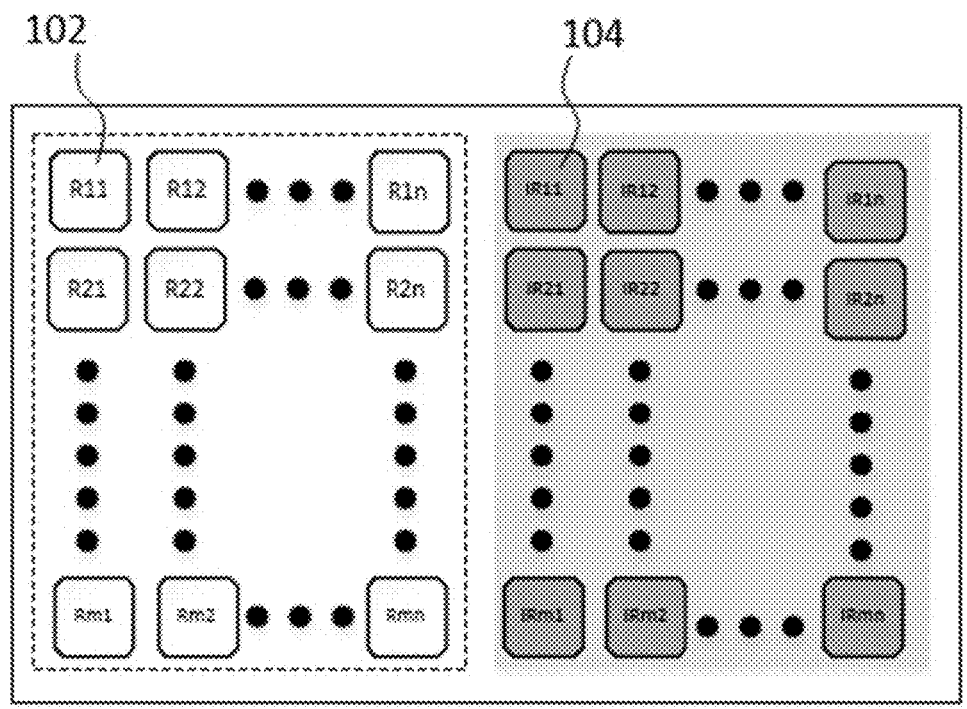
FIGS. 12-14 are structural drawings of three embodiments in term of a layout structure of the light-emitting units of the light-emitting light source of the light receiving device of the present invention.

As shown in FIG. 12, the light-emitting light source 921 of the light-emitting light source device 92 comprises a plurality of first light-emitting units which is placed at equal or unequal intervals to form a m*n first row and column light source array, and a plurality of second light-emitting units which is placed at equal or unequal intervals to form a m*n second row and column light source array, wherein n is an integer greater than 1, and m is an integer greater than or equal to 1. Each first light-emitting unit is a red LED 102, wherein R represents red light in drawings. The first row and column light source array is a red LED array composed of red LEDs. Each second light-emitting unit is an infrared LED 104, wherein the IR represents infrared light in drawings. The second row and column light source array is an infrared light LED array composed of infrared LEDs.

Figure 13:
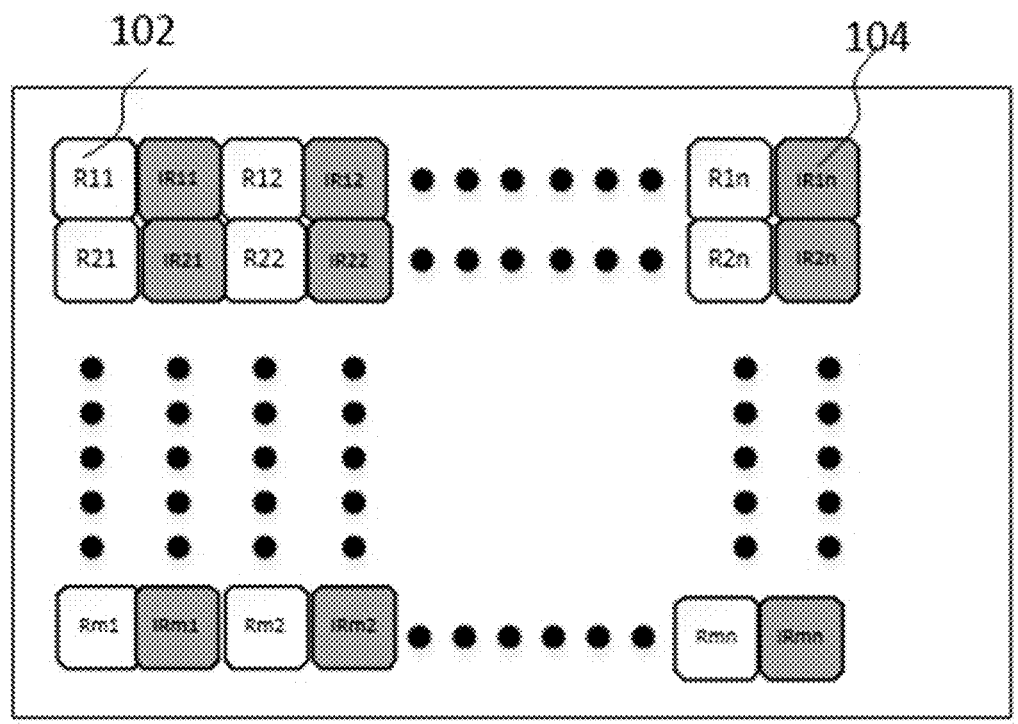

As shown in FIG. 13, the light-emitting light source of the light-emitting light source device comprises a plurality of first light-emitting units and a plurality of second light-emitting units, which are placed at equal or unequal intervals to form a row and column light source array of m rows and 2*n columns, wherein each column of the row and column light source array is a first light-emitting unit column composed of the first light-emitting units or a second light-emitting unit column composed of the second light-emitting units. The first light-emitting unit columns and the second light-emitting unit columns are alternately arranged, wherein n is an integer greater than 1, and m is an integer greater than or equal to 1. However, the optical paths of red or infrared light of two different wavelengths passing through the abdomen of the pregnant woman to the fetus are closer than that in FIG. 12. Obviously, it is also possible to arrange the first light-emitting units and the second light-emitting units in rows alternately, i.e., the plurality of first light-emitting units and the plurality of second light-emitting units are placed at equal or unequal intervals to form a row and column light source array of 2*m rows and n columns, wherein each row of the row and column light source array is a first light-emitting unit row composed of the first light-emitting units or a second light-emitting unit row composed of the second light-emitting units. The first light-emitting unit rows and the second light-emitting unit rows are alternately arranged, wherein n is an integer greater than or equal to 1, and m is an integer greater than 1.

Figure 14:
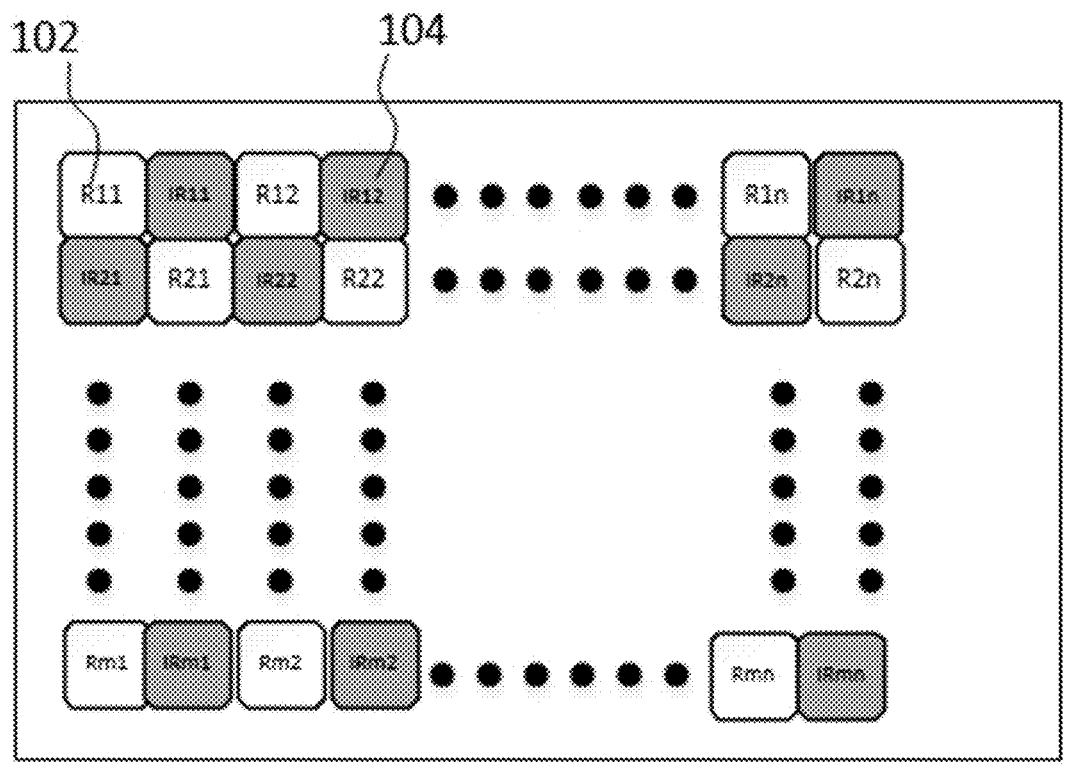

As shown in FIG. 14, in a preferred embodiment of the light-emitting light source device of the present invention, in the row and column light source array composed of the plurality of first light-emitting units and the plurality of second light-emitting units, the first light-emitting units and the second light-emitting units are arranged alternately, such that the first light-emitting units and the second light-emitting units in each row of the row and column light source array are alternately arranged and the first light-emitting units and the second light-emitting units in each column of the row and column light source array are also arranged alternately. The light paths of red or infrared light of two different wavelengths passing through the abdomen of the pregnant woman to the fetus are closer than that in FIG. 13, which greatly improves the intensity and accuracy of the signals collected by the light receiving device 91.

Figure 15:
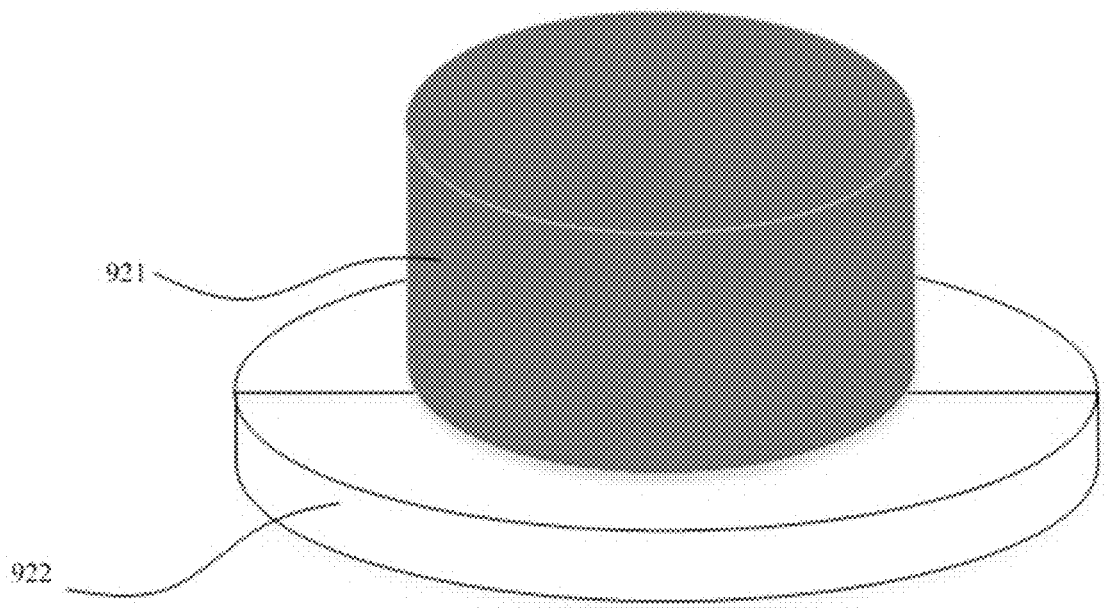
FIG. 15 is a structural schematic diagram of the light-emitting light source device of the present invention.

Further, as shown in FIG. 15, in a preferred embodiment of the light-emitting light source device of the present invention, a light diffusion lens 922 having a diffused irradiation area is placed outside the row and column light source array composed of the plurality of first light-emitting units and the plurality of second light-emitting units of the light-emitting light source 921 so as to increase the luminous power of the light-emitting units while not increasing the luminous radiation per unit irradiation area. Preferably, the light diffusion lens 922 is a concave lens, and the distance between the concave lens and each of the first light-emitting unit and the second light-emitting unit is greater than 0; or, the light diffusion lens is a convex lens, and a distance between the concave lens and each of the first light-emitting unit and the second light-emitting unit is greater than 0 and less than or equal to a focal length of the convex lens.

Further, a preferred embodiment of the fetal blood oxygen optical signal collection device of the present invention, the light receiving device 91 including a plurality of light receivers 204 of the present invention is combined with the light-emitting light source device 92 of the row and column light source array. As a preferred manner, the light receiving device 91 and the light-emitting light source device 92 are mounted on the photosensor mounting mechanism 93. The light-emitting light source of the light-emitting light source device 92 comprises a row and column light source array composed of the plurality of first light-emitting units and the plurality of second light-emitting units. In the row and column light source array, the first light-emitting units and the second light-emitting units are arranged alternately, such that the first light-emitting units and the second light-emitting units in each row of the row and column light source array are alternately arranged, and the first light-emitting units and the second light-emitting units in each column of the row and column light source array are also arranged alternately. In addition, the plurality of the light receivers 204 of the light receiving device 91 is placed round the light-emitting light source device 92 to form a circular shape. The photosensor mounting mechanism 93 is capable of being buckled on the abdomen of the pregnant woman in a dome shape. The light-emitting light source of the light-emitting light source device 92 is located in the middle of the dome, i.e., in the middle of the top side of the abdomen of the pregnant woman. The plurality of light receivers 204 of the light receiving device 91 is placed around the side surface of the abdomen of the pregnant woman to form a circular shape. The light-emitting light source and the plurality of light receivers 204 form a dome shape. Therefore, the illumination of the light source and the collection of the light receivers 204 are implemented at a plurality of points which are not required necessarily to correspond one by one, such that the unit area is increased, and the optical paths of red or infrared light of the two different wavelengths passing through the abdomen of the pregnant woman to the fetus are closer. Therefore, the intensity of the fetal blood flow-related optical signals in the received signals is greatly improved.

Figure 16:
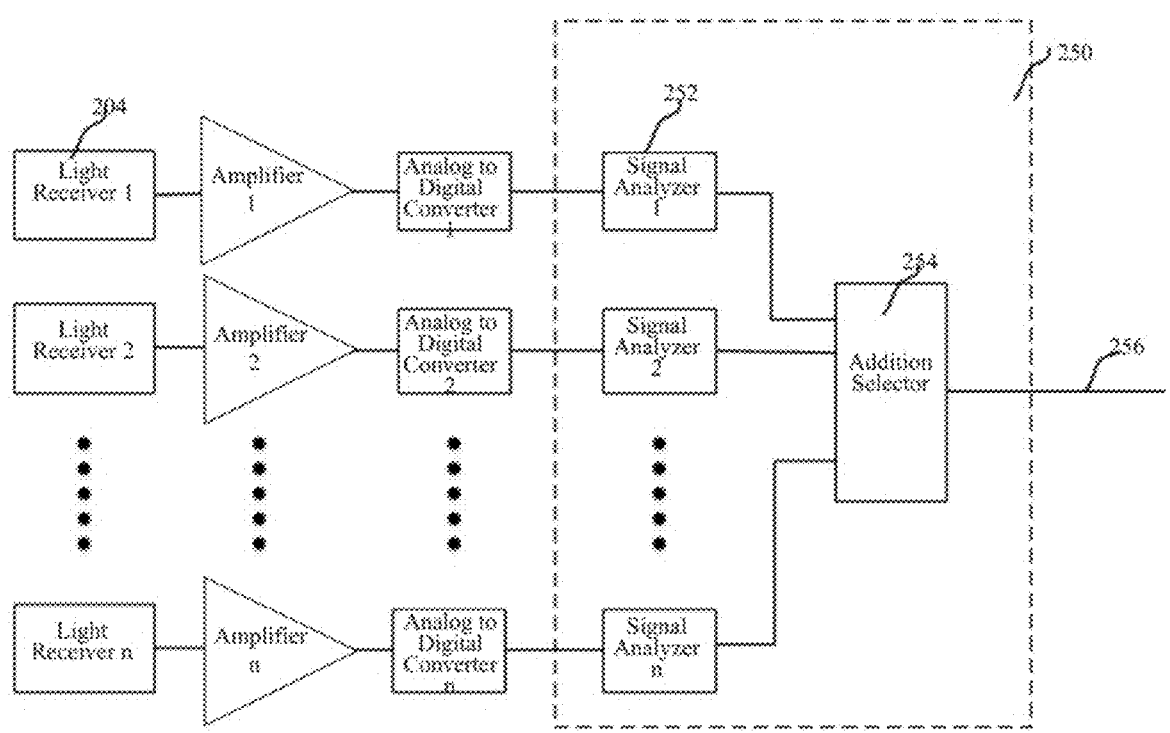
FIG. 16 is a structural drawing of another embodiment of the light receiving device of the present invention.

As shown in FIG. 16, as another improvement of the present invention, the light receiving device 91 of the present invention comprises a plurality of light receivers 204, and a primary signal processor 250 connected to the plurality of light receivers 204. The primary signal processor 250 comprises an interface which is used for receiving a fetal heart rate signal and connected to the fetal heart rate collection device. The primary single processor 250 is configured to receive a plurality of optical signals related to the fetal blood oxygen saturation through the plurality of light receivers 204, acquire the fetal heart rate signals collected at the same time through the fetal heart rate collection device, and perform correlation analysis on the plurality of received optical signals related to fetal blood oxygen saturation and the fetal heart rate signals to obtain correlation coefficients of the respective optical signals; obtain corresponding weighting coefficients of the optical signals based on the correlation coefficients; and superimposing the plurality of optical signals according to the respective weighting coefficients to obtain an optical signal sum.

The present invention also provides a trans-abdominal non-invasive fetal blood oxygen saturation detection signal processing method in which a plurality of received optical signals including fetal blood oxygen saturation information is synthesized into an optical signal sum, such that the intensity of the optical signals related to the fetal blood oxygen saturation is improved, and the noise interference is eliminated to increase the signal to noise ratio. The method may be used for a light receiving device 91 and comprises the following steps:

performing correlation analysis on the plurality of received optical signals related to the fetal blood oxygen saturation and the fetal heart rate signals respectively to obtain correlation coefficients of the respective optical signals; obtaining corresponding weighting coefficient of the optical signals based on the correlation coefficients; and superimposing the plurality of optical signals according to the respective weighting coefficients to obtain an optical signal sum. The step of obtaining the corresponding weighting coefficient of the optical signals based on the correlation coefficients includes: discarding the optical signal, i.e., setting the weighting coefficient as 0 if the correlation coefficient of each optical signal is less than a preset correlation threshold; obtaining the weighting coefficient according to the correlation coefficient if the correlation coefficient is greater than the preset correlation threshold, wherein the greater the correlation coefficient, the greater the weighting coefficient, and the weighting coefficient is greater than 0 and less than 1; and then, superimposing the plurality of optical signals according to the respective weighing coefficients to obtain the optical signal sum, for example, multiplying each of the plurality of optical signals by the respective weighting coefficient and superimposing to obtain the optical signal sum. In the trans-abdominal non-invasive fetal blood oxygen saturation detection signal processing method of the present invention, the plurality of light receivers 204 is configured to collect a plurality of optical signals related to the fetal blood oxygen saturation, superimpose and synthesize the optical signals into the optical signal sum to improve the intensity of the optical signals, perform correlation analysis on the optical signals collected by the plurality of light receivers 204 and the fetal heart rates collected at the same time, and then weight and superimpose the same to eliminate noise signal interference unrelated to the fetal blood oxygen saturation in the optical signals, such that the signal to noise ratio of the collected optical signals is increased to improve the accuracy and reliability of the trans-abdominal fetal blood oxygen saturation detection.

The trans-abdominal non-invasive fetal blood oxygen saturation detection signal processing method of the present invention may be used for the light receiving device 91 of the trans-abdominal non-invasive fetal blood oxygen saturation detection device. A plurality of received optical signals related to the fetal blood oxygen saturation is selected and superimposed to obtain an optical signal sum to eliminate the noise interference and increase the signal to noise ratio. Then, the optical signal sum related to the fetal blood oxygen saturation is transmitted to the signal processing controller 11 of the trans-abdominal fetal oximeter 1. The signal processing controller 11 analyzes and calculates the optical signal sum and the fetal heart rate signals to obtain the fetal blood oxygen saturation. Of course, the signal processing controller 11 may further analyze and calculate based on the optical signal sum, and the collected pregnant woman heart rate, and/or the pregnant woman optical signal, and/or the fetal heart rate to obtain the fetal blood oxygen saturation. The calculation method of the fetal blood oxygen saturation has been described in inventor's another patent CN201310182965.2, and is not described herein again. It should be noted that, the trans-abdominal non-invasive fetal blood oxygen saturation detection signal processing method of the present invention may also be processed by the signal processing controller 11, and the signal processing controller 11 receives the plurality of optical signals and synthesizes the same into the optical signal sum, which, however, will greatly increase the complexity of the system.

As shown in FIG. 16, the light receiving device 91 of the present invention comprises a plurality of light receivers 204, a plurality of amplifiers connected to the plurality of light receivers 204 respectively, a plurality of digital-to-analog converters connected to the plurality of amplifiers, and a primary signal processor 250 connected to the plurality of digital-to-analog converters. The primary signal processor 250 is connected to an output end of the fetal heart rate collection device. Each of the light receivers 204 receives optical signals from the abdominal cavity of the pregnant woman and converts them into a plurality of electrical signals. The plurality of electrical signals are then processed into a plurality of digital signals by the amplifiers and the analog-to-digital converters, then processed by the primary signal processor 250, and then synthesized into a received optical signal sum 256.

An embodiment of the primary signal processor 250, as shown in FIG. 16, comprises a plurality of signal analyzers 252 and an addition selector 254 connected to the plurality of signal analyzers 252, wherein the plurality of signal analyzers 252 is configured to perform correlation analysis, and the addition selector 254 is configured to perform selective superposition on the signals. Of course, the primary signal processor 250 may be a single chip microcomputer. The trans-abdominal non-invasive fetal blood oxygen saturation detection signal processing method of the present invention is implemented by software. The corresponding functions including the signal analyzers 252 and the addition selector 254 are implemented by software. The single-chip microcomputer executes the corresponding software, analyzes, processes and superimposes the plurality of optical signals to realize the synthesis of the optical signal sum. A fetal heart rate sensor of the fetal heart rate collection device may be a Doppler ultrasound fetal heart sound sensor, or a fetal electrocardiography sensor composed of electrodes, or other fetal heart rate sensor. As another embodiment, the primary signal processor 250 may be a single chip microcomputer which, instead of the adder of the embodiment shown in FIGS. 4-5, implements the embodiment shown in FIGS. 4-5, and directly superimposes the signals directly through software.

Figure 17:
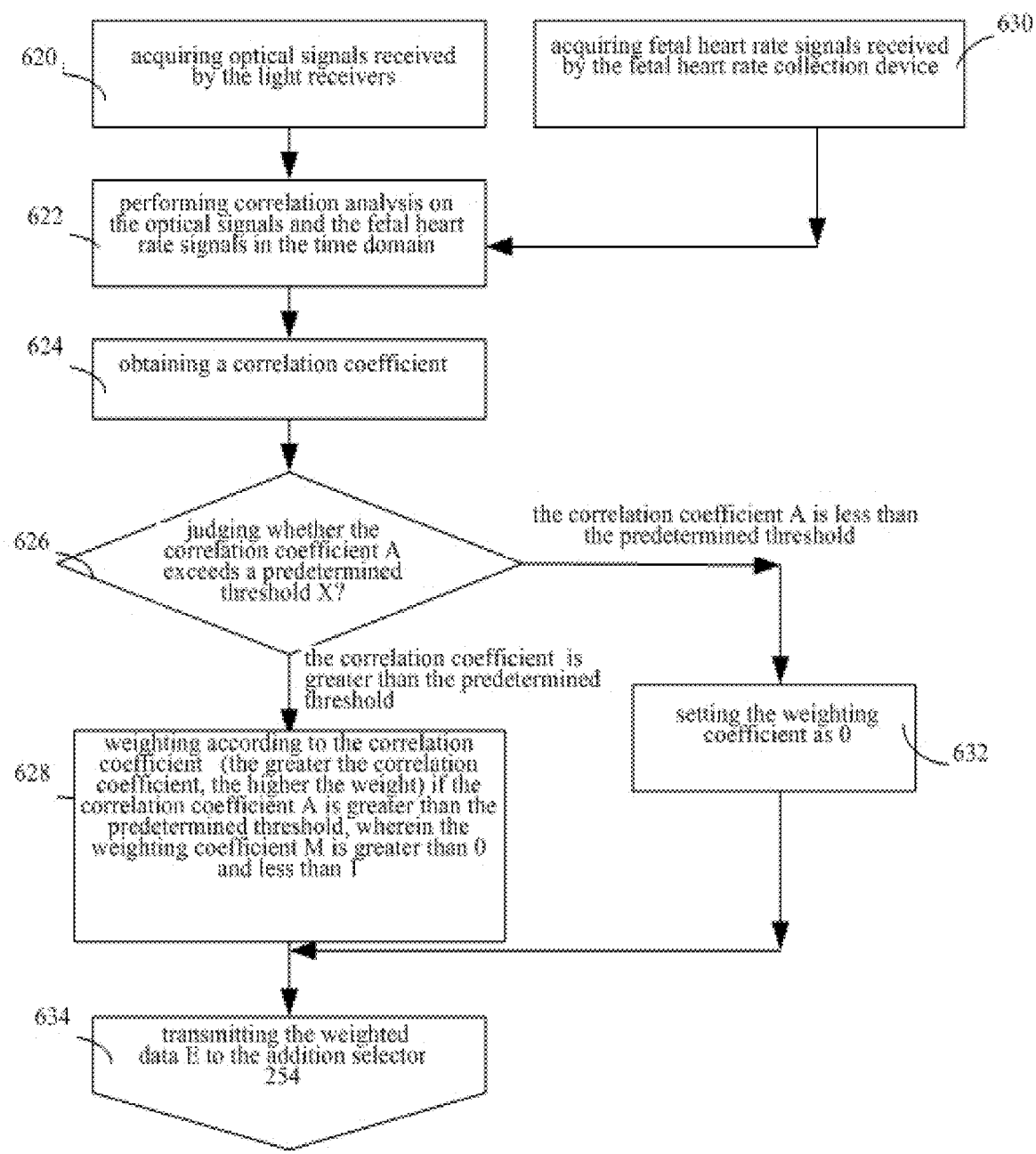
FIG. 17 is a block diagram of an embodiment of a signal processing flow of a primary processor 250 shown in FIG. 16.

FIG. 17 is an example of a signal analysis flow of a signal analyzer 252 in a time domain during signal analysis. The signal analyzer 252 is a time domain signal analyzer, and is configured to perform correlation analysis on each received optical signal related to the fetal blood oxygen saturation and the received fetal heart rate signal in the time domain to obtain a correlation coefficient of each optical signal. Referring to FIG. 17 for details, in the trans-abdominal non-invasive fetal blood oxygen saturation detection signal processing method of the present invention, the flow of superimposing and synthesizing the weights of the digital signals of the plurality of optical signals into the received optical signal sum comprises the following steps:

(620) acquiring optical signals received by the light receivers, converting the optical signals received by the light receivers into electrical signals, processing the electrical signals and converting the same into digital signals through the amplifiers and the digital-to-analog converters to obtain optical signals related to the fetal blood oxygen saturation;

(630) in parallel with step (620), acquiring fetal heart rate signals received by the fetal heart rate collection device;

(622) performing correlation analysis on the optical signals and the fetal heart rate signals in the time domain, wherein a correlation analysis algorithm belongs to the prior art and is described in the general mathematics manual, and will not be described here;

(624) calculating a correlation coefficient A through correlation analysis;

(626) judging whether the correlation coefficient A exceeds a predetermined threshold X, proceeding to step 628 if the correlation coefficient A is greater than the predetermined threshold X, or proceeding to step 632 if the correlation coefficient A is less than the predetermined threshold X;

(628) obtaining a weighting coefficient M according to the correlation coefficient A, and then proceeding to step 634 below, wherein the weighting coefficient M is greater than 0 and less than 1;

(632) setting the weighting coefficient M as 0, and then proceeding to step 634 below; and (634) multiplying the optical signal related to the fetal blood oxygen saturation by the weighting coefficient M and weighting, and transmitting the weighted data E to the addition selector 254.

Figure 18:
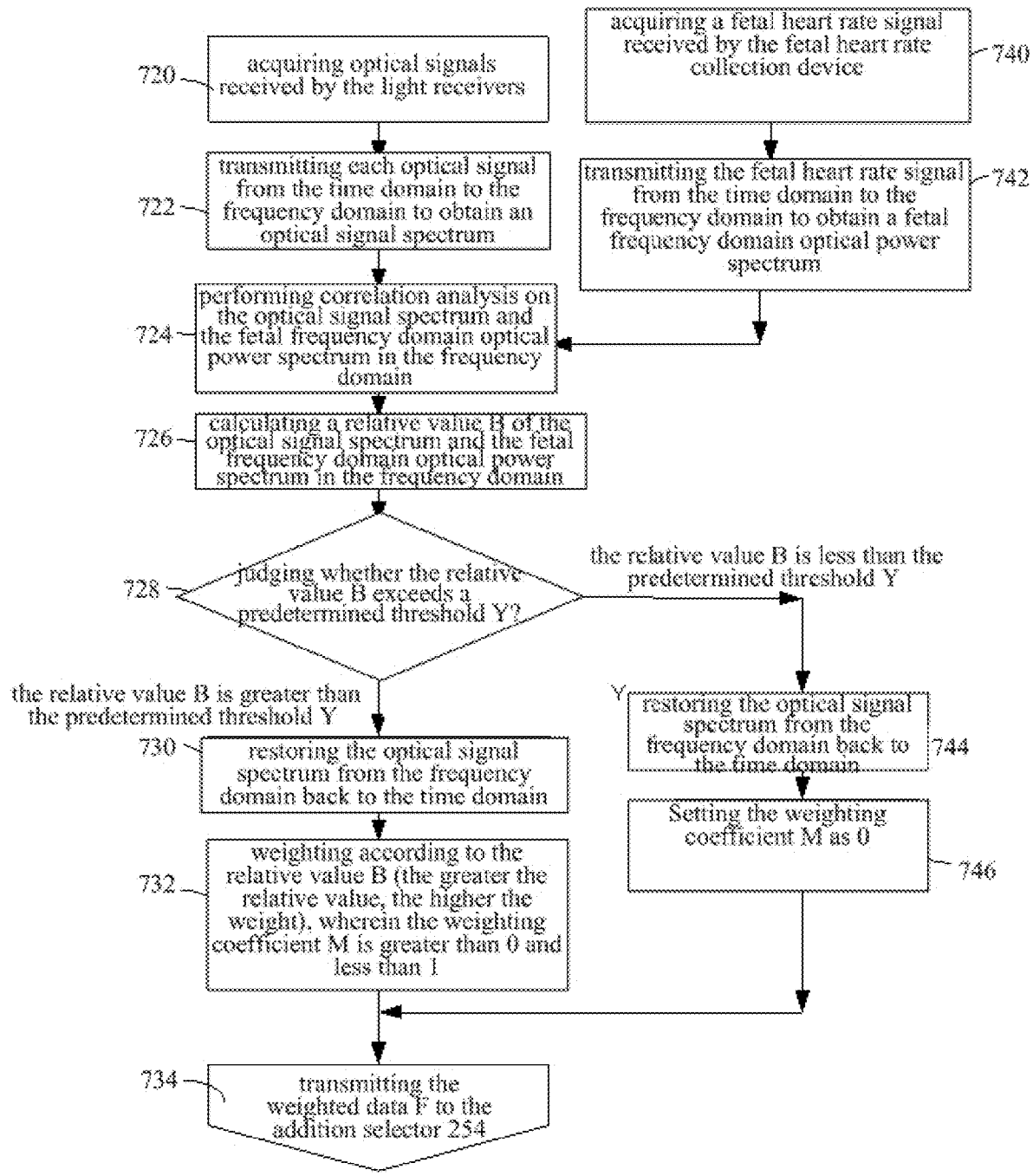
FIG. 18 is a block diagram of another embodiment of the signal processing flow of the primary processor 250 shown in FIG. 16.

FIG. 18 is an example of a signal analysis flow of a signal analyzer 252 in a frequency domain during signal analysis. The signal analyzer 252 is a frequency domain signal analyzer which is configured to transmit each received optical signal related to the fetal blood oxygen saturation from the time domain to the frequency domain to obtain an optical signal spectrum, meanwhile transmit the received fetal heart rate signal from the time domain to the frequency domain to obtain a fetal frequency domain optical power spectrum, and perform correlation analysis on the optical signal spectrum and the fetal frequency domain optical power spectrum in the frequency domain to obtain a correlation coefficient of each optical signal. Referring to FIG. 18 for details, in the trans-abdominal non-invasive fetal blood oxygen saturation detection signal processing method of the present invention, the flow of superimposing and synthesizing the weights of a plurality of digital signal into the received optical signal sum 256 comprises the following steps:

(720) acquiring optical signals received by the light receivers, converting the optical signals received by the light receivers into electrical signals, processing the electrical signals and converting the same into digital signals through the amplifiers and the digital-to-analog converters to obtain optical signals related to the fetal blood oxygen saturation, and then proceeding to step 722 below;

(722) transmitting each optical signal related to the fetal blood oxygen saturation from the time domain to the frequency domain to obtain an optical signal spectrum, and then proceeding to step 724;

(740) in parallel with step 720, acquiring a fetal heart rate signal received by the fetal heart rate collection device, and then proceeding to step 742 below;

(742) transmitting the input fetal heart rate signal from the time domain to the frequency domain to obtain a fetal frequency domain optical power spectrum, and then proceeding to step 724;

(724) performing correlation analysis on the optical signal spectrum related to the fetal blood oxygen saturation and the fetal frequency domain optical power spectrum in the frequency domain;

(726) calculating a relative value B of the optical signal spectrum and the fetal frequency domain optical power spectrum in the frequency domain as a correlation coefficient through correlation analysis;

(728) judging whether the relative value B exceeds a predetermined threshold Y, proceeding to step 730 below if the relative value B is greater than the predetermined threshold Y, and proceeding to step 744 if the relative value B is less than the predetermined threshold Y;

(730) restoring the optical signal spectrum from the frequency domain back to the time domain, and then proceeding to step 732 below;

(732) obtaining a weighting coefficient M according to the relative value B, and then proceeding to step 734 below, wherein the weighting coefficient M is greater than 0 and less than 1;

(744) restoring the optical signal spectrum from the frequency domain back to the time domain, and then proceeding to step 746 below, of course, step 744 can also be omitted;

(746) setting the weighting coefficient M as 0, and then proceeding to step 734 below; and (734) weighting the optical signal related to the fetal blood oxygen saturation and the weighting coefficient M, and transmitting the weighted data F to the addition selector 254.

Figure 19:
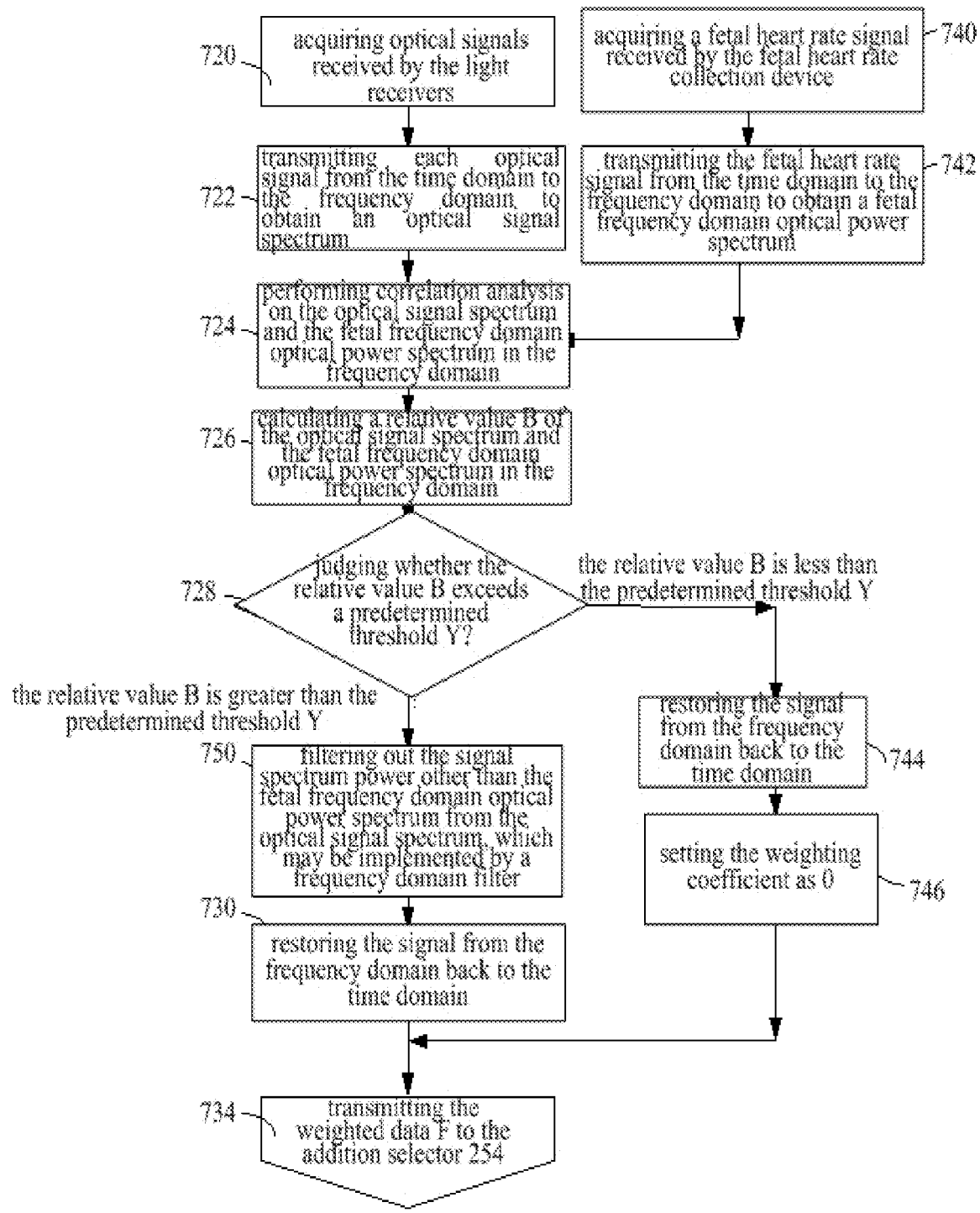
FIG. 19 is a block diagram of yet another embodiment of the signal processing flow of the primary processor 250 shown in FIG. 16.

FIG. 19 is another example of a signal analysis flow of a signal analyzer 252 in a frequency domain. The signal analyzer 252 is configured to transmit each received optical signal related to the fetal blood oxygen saturation from the time domain to the frequency domain to obtain an optical signal spectrum, meanwhile transmit the received fetal heart rate signal from the time domain to the frequency domain to obtain a fetal frequency domain optical power spectrum, perform correlation analysis on the optical signal spectrum and the fetal frequency domain optical power spectrum in the frequency domain to obtain a correlation coefficient of each optical signal, filter out a signal spectrum power other than the fetal spectrum power from the optical signal spectrum to obtain a filtered optical signal spectrum so as to eliminate the noise signal interference unrelated to the fetal blood oxygen saturation in the optical signals, and then restore the filtered optical signal spectrum from the frequency domain back to the time domain to obtain a filtered optical signal as a weighted superimposed optical signal. Referring to FIG. 19 for details, in the trans-abdominal non-invasive fetal blood oxygen saturation detection signal processing method of the present invention, the flow of superimposing and synthesize the weights of the plurality of digital signals into the received optical signal sum comprises the following steps:

(720) acquiring optical signals received by the light receivers, converting the optical signals received by the light receivers into electrical signals, processing the electrical signals and converting the same into digital signals through the amplifiers and the digital-to-analog converters to obtain optical signals related to the fetal blood oxygen saturation, and then proceeding to step 722 below;

(722) transmitting each optical signal related to the fetal blood oxygen saturation from the time domain to the frequency domain to obtain an optical signal spectrum, and then proceeding to step 724 below;

(740) in parallel with step 720, acquiring a fetal heart rate signal received by the fetal heart rate collection device, and then proceeding to step 742 below;

(742) transmitting the input fetal heart rate signal from the time domain to the frequency domain to obtain a fetal frequency domain optical power spectrum, and then proceeding to step 724;

(724) performing correlation analysis and comparison on the optical signal spectrum related to the fetal blood oxygen saturation and the fetal frequency domain optical power spectrum in the frequency domain;

(726) calculating a relative value B of the optical signal spectrum and the fetal frequency domain optical power spectrum in the frequency domain as a correlation coefficient through correlation analysis;

(728) judging whether the relative value B exceeds a predetermined threshold Y, proceeding to step 750 below if the relative value B is greater than the predetermined threshold Y, or proceeding to step 744 below if the relative value B is less than the predetermined threshold Y;

(750) filtering out the signal spectrum power other than the fetal frequency domain optical power spectrum from the optical signal spectrum to obtain a filtered optical signal spectrum, which may be implemented by a frequency domain filter or by software, and then proceeding step 730 below;

(730) restoring the filtered optical signal spectrum from the frequency domain back to the time domain to obtain a filtered optical signal as a weighted superimposed optical signal, and then proceeding step 734 below;

(744) restoring the optical signal spectrum from the frequency domain back to the time domain, and then proceeding to step 746 below;

(746) setting the weighting coefficient M as 0, and then proceeding to step 734 below;

(734) weighting the filtered optical signal related to the fetal blood oxygen saturation and the weighting coefficient M, and transmitting the weighted data F to the addition selector 254.

It should be noted that FIG. 18 differs from FIG. 19 in that: after a frequency domain signal is determined to exceed the predetermined threshold Y in step 728, the inverse conversion is performed in step 730 directly in FIG. 18 to restore a time domain signal. However, in FIG. 19, the frequency domain signals from which signals unrelated to the fetal frequency domain optical power spectrum are filtered out are inputted to step 730 for inverse conversion to restore the time domain signals.

The mathematical conversion formula for converting the signal from the time domain to the frequency domain in step 722 in FIG. 18 and FIG. 19 may adopt a fast Fourier transform formula or a Z transform formula. In addition, the Laplace transform may also be used for the conversion from the time domain to the domain frequency. The conversion manner from the time domain to the frequency domain falls into the prior art and will not be repeated.

The mathematical conversion formula for inversely converting the signal from the frequency domain to the time domain in step 730 in FIG. 18 and FIG. 19 may adopt a fast inverse Fourier transform formula or an inverse Z transform formula or an inverse Laplace transform. The inverse conversion manner from the frequency domain to the time domain falls into the prior art and will not be repeated.

Figure 20:
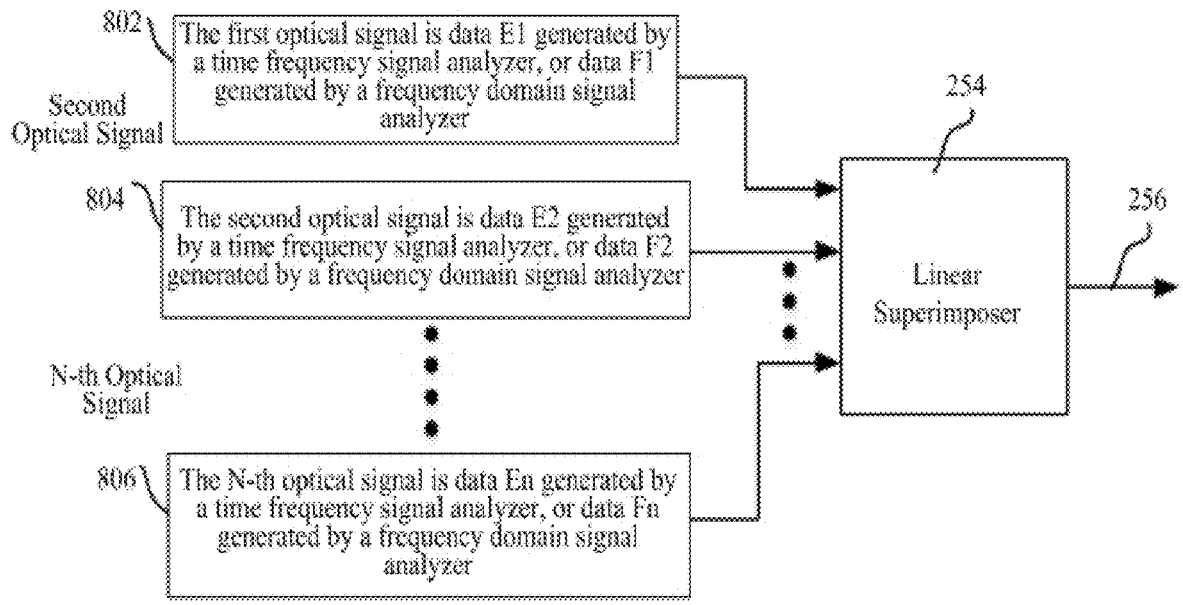
FIG. 20 is an embodiment of an addition selector of the light receiving device of FIG. 16.
Figure 21:
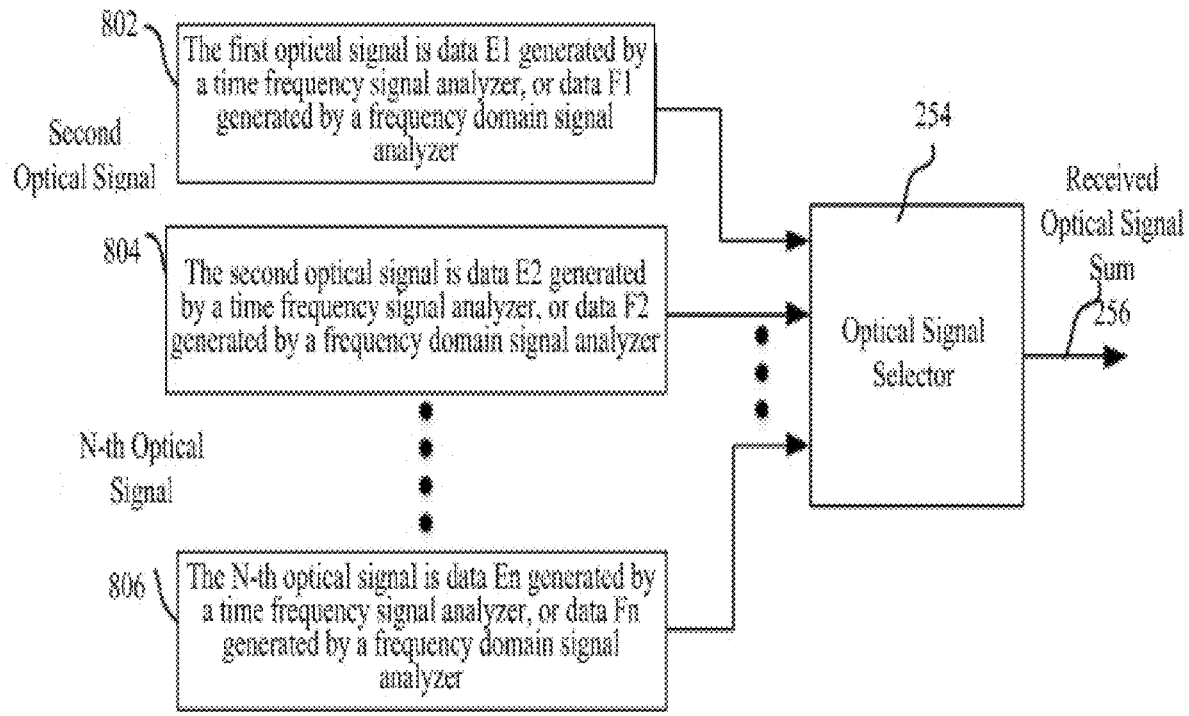
FIG. 21 is another embodiment of the addition selector of the light receiving device of FIG. 16.

Referring to FIGS. 16, 20-21, the primary signal processor 250 further includes a time-frequency converter for converting a digital signal from the time domain to the frequency domain and/or a time-frequency inverse converter for restoring the digital signal from the frequency domain to the time domain. The signal analyzer 252 of the primary signal processor 250 is configured to label a weighting coefficient for each digital signal based on the correlation between the fetal heart rate signal and the digital signal in the frequency domain or in the time domain. The addition selector 254 is configured to perform superimposition processing according to the weighting coefficient. The addition selector 254 may be a linear superimposer or an optical signal selector.

FIG. 20 is a flow example of the addition selector 254 in FIG. 16. The primary signal processor 250 includes an addition selector 254. The addition selector 254 is a linear superimposer that linearly superimposes a plurality of digital signals outputted by the light receivers 204 and analyzed by the signal analyzers 252 to synthesize the received optical signal sum 256. Specifically, signals 802, 804, 806 generated by each of the signal analyzers 252 are introduced into a linear superimposer for linear superposition to produce the received optical signal sum 256. The received optical signal sum 256 will be sent to the trans-abdominal fetal oximeter 1 via a communication link 14. The signals inputted by the linear superimposer of the primary signal processor 250 is the data E generated by the time domain signal analyzer or the data F generated by the frequency domain signal analyzer.

FIG. 21 is another flow example of the addition selector 254 in FIG. 16. The primary signal processor 250 includes an addition selector 254. The addition selector 254 is an optical signal selector that selects one of a plurality of digital signals outputted by the light receivers 204 and analyzed by the signal analyzers 252 as the received optical signal sum 256; or selects a plurality of digital signals and superimposes the same to form the received optical signal sum 256. Specifically, the signals 802, 804, 806 generated by each of the signal analyzers are introduced into the optical signal selector for further screening and superimposing. The optical signal selector 810 makes a determination according to the comparison of all the signals 802, 804 and 806, the cognition for the positions of each light receiver 204 as well as other knowledge related to the fetal blood oxygen saturation and selects one or more signals to generate the received optical signal sum 256. The received optical signal sum 256 will be sent to the trans-abdominal fetal oximeter 1 via a communication link 14. The signals outputted by the optical signal selector of the primary signal processor 250 is the data E generated by the time domain signal analyzer or the data F generated by the frequency domain signal analyzer. The selection conditions for the optical signal selector of the primary signal processor 250 include a blood oxygen saturation signal state, and/or a position signal state The detection device of the present invention can be used not only for fetuses with poor heart rate caused by hypoxia, but also for fetuses with normal heart rate. The detection device can be used for detection in hospitals, and can also be transplanted and extended to remote perinatal monitoring supported by mobile internet, such as by remote household detection. The detection device of the present invention can be combined with an existing Electronic Fetal Monitor (EFM) to achieve more comprehensive signal processing for a novel fetal monitoring device.

The above content is the further detailed description made to the present invention in conjunction with the specific preferred embodiments, but will not thereby considered that the specific implementations of the present invention are only limited to these descriptions. For those skilled in the art to which the present invention belongs, several simple deductions or replacements may also be made without departing from the concept of the present invention, all of which should be considered to fall into the protection scope of the present invention.

The invention claimed is:

1. A trans-abdominal non-invasive fetal blood oxygen saturation detection device, comprising a trans-abdominal fetal oximeter and a signal detection assembly connected to the trans-abdominal fetal oximeter, wherein the trans-abdominal oximeter comprises a signal processing controller; the signal detection assembly comprises a light-emitting light source device, a light receiving device for collecting an optical signal related to the fetal blood oxygen saturation from the outside of the abdominal cavity of a pregnant woman, and a reference signal detection device for collecting a fetal heart rate signal; the light-emitting light source device, the light receiving device and the reference signal detection device are all connected to the signal processing controller, wherein the light-emitting light source device is configured to irradiate two or more different wavelengths of light into the abdominal cavity of the pregnant woman;

the light receiving device comprises a plurality of light receivers respectively configured to be placed at a plurality of different positions outside the abdominal cavity of the pregnant woman, and is configured to collect a plurality of optical signals related to the fetal blood oxygen saturation through the plurality of light receivers, synthesize the optical signals into an optical signal sum related to the fetal blood oxygen saturation and then outputs it to the signal processing controller;

the signal processing controller is configured to calculate the fetal blood oxygen saturation according to the optical signal sum outputted by the light receiving device, and according to the fetal heart rate signal which is collected from the reference signal detection device, the light receiving device is configured to synthesize the plurality of optical signals related to the fetal blood oxygen saturation into an optical signal sum through the following steps:

step A: performing correlation analysis on the plurality of received optical signals and the fetal heart rate signal respectively to obtain correlation coefficients of the respective optical signals;

step B: obtaining corresponding weighting coefficients of the optical signals based on the correlation coefficients; and step C: superimposing the plurality of optical signals according to the respective weighting coefficients to obtain an optical signal sum related to the fetal blood oxygen saturation.

2. The trans-abdominal non-invasive fetal blood oxygen saturation detection device according to claim 1, wherein the light receiving device comprises a plurality of light receivers and a primary signal processor connected to the plurality of light receivers, wherein the primary signal processor comprises an interface for receiving the fetal heart rate signal.

3. The trans-abdominal non-invasive fetal blood oxygen saturation detection device according to claim 2, wherein the primary signal processor comprises a plurality of signal analyzers and an addition selector connected to the plurality of signal analyzers, wherein the plurality of signal analyzers are configured to analyze correlation coefficients of the optical signals related to the fetal blood oxygen saturation, which are collected by the plurality of light receivers, and the fetal heart rate signals respectively, and the addition selector is configured to superimpose the weights of a plurality of digital signals according to the analysis results from the plurality of signal analyzers and synthesize the same into an optical signal sum.

4. The trans-abdominal non-invasive fetal blood oxygen saturation detection device according to claim 2, wherein the primary signal processor is a single chip microcomputer.

5. The trans-abdominal non-invasive fetal blood oxygen saturation detection device according to claim 1, wherein the step B comprises: setting the weighting coefficient as 0 if the correlation coefficient of each optical signal is less than a preset correlation threshold; obtaining the weighting coefficient according to the correlation coefficient if the correlation coefficient is greater than the preset correlation threshold, and superimposing the plurality of optical signals according to the respective weighting coefficients to obtain the optical signal sum.

6. The trans-abdominal non-invasive fetal blood oxygen saturation detection device according to claim 1, wherein the step A comprises: performing correlation analysis on each received optical signal related to the fetal blood oxygen saturation and the received fetal heart rate signal in a time domain to obtain the correlation coefficient of each optical signal.

7. The trans-abdominal non-invasive fetal blood oxygen saturation detection device according to claim 1, wherein the step A comprises: transmitting each received optical signal related to the fetal blood oxygen saturation from the time domain to a frequency domain to obtain an optical signal spectrum, and meanwhile transmitting the received fetal heart rate signal from the time domain to the frequency domain to obtain a fetal frequency domain optical power spectrum; and performing correlation analysis on the optical signal spectrum and the fetal frequency domain optical power spectrum in the frequency domain to obtain the correlation coefficient of each optical signal.

8. The trans-abdominal non-invasive fetal blood oxygen saturation detection device according to claim 7, wherein the step A further comprises: filtering out a signal spectrum power other than the fetal spectrum power from the optical signal spectrum to obtain a filtered optical signal spectrum, and restoring the filtered optical signal spectrum from the frequency domain back to the time domain to obtain a filtered optical signal as a weighted superimposed optical signal.

9. The trans-abdominal non-invasive fetal blood oxygen saturation detection device according to claim 1, comprising a fetal blood oxygen optical signal collection device integrated with the light-emitting light source device and the light receiving device, wherein the fetal blood oxygen optical signal collection device comprises a photosensor mounting mechanism on which the light-emitting light source device and the light receiving device comprising a plurality of light receivers are integrally mounted.

10. The trans-abdominal non-invasive fetal blood oxygen saturation detection device according to claim 9, wherein the plurality of light receivers of the light receiving device is placed around a light-emitting light source of the light-emitting light source device to form a circular shape.

11. The trans-abdominal non-invasive fetal blood oxygen saturation detection device according to claim 9, wherein the plurality of light receivers of the light receiving device is placed around a light-emitting light source of the light-emitting light source device to form a square shape; or the plurality of light receivers of the light receiving device forms an array of i rows*j columns and is placed on one side of the light-emitting light source of the light-emitting light source device, both i and j being integers greater than 0; or the plurality of light receivers of the light receiving device forms two arrays of i rows*j columns and is placed on two sides of the light-emitting light source of the light-emitting light source device respectively, both i and j being integers greater than 0.

12. The trans-abdominal non-invasive fetal blood oxygen saturation detection device according to claim 1, wherein the fetal blood oxygen optical signal collection device further comprises a conduction switch controlled by a signal generated by a pulse timing sequence emitted by the light-emitting light source device, wherein an optical signal received by each of the light receivers of the light receiving device is converted into an electrical signal which is then passed through the conduction switch, such that the illumination of the light-emitting light source device and the received optical signal passed through the conduction switch are synchronized, and only the optical signal synchronized with the illumination of the light-emitting light source device within a narrow pulse time can be transmitted to an analog-to-digital converter of the light receiving device and converted into a digital signal for further processing.

13. The trans-abdominal non-invasive fetal blood oxygen saturation detection device according to claim 1, wherein the light-emitting light source device comprises a light-emitting light source and a light source driver connected to the light-emitting light source, wherein the light source driver is connected to the signal processing controller, and the light source driver is configured to drive the light-emitting light source to emit pulsed light having a frequency higher than 20 Hz under the control of the signal processing controller, a duty ratio of the pulse of the pulsed light being less than 40%.

14. The trans-abdominal non-invasive fetal blood oxygen saturation detection device according to claim 1, wherein the light-emitting light source device comprises a light-emitting light source comprising a plurality of first light-emitting units and a plurality of second light-emitting units, wherein each of the plurality of first light-emitting units is capable of emitting red or infrared light of a first wavelength, and each of the plurality of second light-emitting units is capable of emitting red or infrared light of a second wavelength, the first wavelength being different from the second wavelength; the number of the first light-emitting units is the same as that of the second light-emitting units; the plurality of first light-emitting units and the plurality of second light-emitting units are placed in a row and column light source array.

15. The trans-abdominal non-invasive fetal blood oxygen saturation detection device according to claim 14, wherein the plurality of first light-emitting units is placed at equal or unequal intervals to form a m*n first row and column light source array, and the plurality of second light-emitting units is placed at equal or unequal intervals to form a m*n second row and column light source array, wherein n is an integer greater than 1, and m is an integer greater than or equal to 1.

16. The trans-abdominal non-invasive fetal blood oxygen saturation detection device according to claim 14, wherein the plurality of first light-emitting units and the plurality of second light-emitting unit are placed at equal or unequal intervals to form a row and column light source array of m rows and 2*n columns, each column of the row and column light source array is a first light-emitting unit column composed of the first light-emitting units or a second light-emitting unit column composed of the second light-emitting units, and the first light-emitting unit columns and the second light-emitting unit columns are alternately arranged, wherein n is an integer greater than 1, and m is an integer greater than or equal to 1 or, the plurality of first light-emitting units and the plurality of second light-emitting unit are placed at equal or unequal intervals to form a row and column light source array of 2*m rows and n columns, each row of the row and column light source array is a first light-emitting unit row composed of the first light-emitting units or a second light-emitting unit row composed of the second light-emitting units, and the first light-emitting unit rows and the second light-emitting unit rows are alternately arranged, wherein n is an integer greater than or equal to 1, and m is an integer greater than 1.

17. The trans-abdominal non-invasive fetal blood oxygen saturation detection device according to claim 14, wherein in the row and line light source array composed of the plurality of first light-emitting units and the plurality of second light-emitting units, the first light-emitting units and the second light-emitting units are alternately arranged such that the first light-emitting units and the second light-emitting units in each row of the row and column light source array are alternately arranged, and the first light-emitting units and the second light-emitting units in each column of the row and column light source array are also alternately arranged.

18. The trans-abdominal non-invasive fetal blood oxygen saturation detection device according to claim 14, wherein a light diffusion lens having a diffused irradiated area is placed outside the row and column light source array composed of the plurality of first light-emitting units and the plurality of second light-emitting units of the light-emitting light source.

* * * * *